United States Patent [19]
Roe et al.

[11] Patent Number: 5,876,391
[45] Date of Patent: Mar. 2, 1999

[54] ABSORBENT ARTICLE WITH STRUCTURAL ELASTIC-LIKE FILM WEB WAIST BELT

[75] Inventors: Donald C. Roe, West Chester; David J. K. Goulait, Cincinnati; Sheila S. Rodriguez, Cincinnati; David W. Cabell, Cincinnati, all of Ohio

[73] Assignee: The Procter & Gamble Company, Cincinnati, Ohio

[21] Appl. No.: 728,469

[22] Filed: Oct. 10, 1996

Related U.S. Application Data

[60] Division of Ser. No. 333,921, Nov. 7, 1994, abandoned, which is a continuation-in-part of Ser. No. 155,406, Nov. 19, 1993, abandoned.

[51] Int. Cl.[6] .................................................. A61F 13/15
[52] U.S. Cl. ........................................ 604/385.2; 604/387
[58] Field of Search .............................. 604/385.1, 385.2, 604/392, 393, 387, 386, 390, 394

[56] References Cited

U.S. PATENT DOCUMENTS

| | | |
|---|---|---|
| 235,449 | 12/1880 | Newton . |
| 659,266 | 10/1900 | Stewart . |
| 728,828 | 5/1903 | Arkell . |

(List continued on next page.)

FOREIGN PATENT DOCUMENTS

| | | |
|---|---|---|
| 956751 | 10/1974 | Canada . |
| 0 307 871 B1 | 12/1992 | European Pat. Off. . |
| 0 567 792 A1 | 11/1993 | European Pat. Off. . |
| 31 76053 | 7/1991 | Japan . |
| 31 95555 | 8/1991 | Japan . |
| 4-28364 | 1/1992 | Japan . |
| 6-6818 | 2/1994 | Japan . |
| 2 244 422 | 4/1991 | United Kingdom . |
| 91 00720 | 1/1991 | WIPO . |
| WO 93/25171 | 12/1991 | WIPO . |
| WO 93/09742 | 5/1993 | WIPO . |

*Primary Examiner*—Mark O. Polutta
*Assistant Examiner*—David J. Cho
*Attorney, Agent, or Firm*—Steven W. Miller; David M. Weirich; Jacobus C. Rasser

[57] ABSTRACT

Absorbent articles such as disposable diapers, incontinent briefs, diaper holders, training pants, feminine hygiene garments and the like, that have a unique waist feature that improves the dynamic fit as well as the containment characteristics of the absorbent article. Such absorbent articles comprise a chassis assembly preferably comprising a liquid pervious topsheet, a liquid impervious backsheet, and an absorbent core positioned between the topsheet and the backsheet; an extensible waist belt; and a closure system for maintaining the absorbent article on the wearer. The extensible waist belt provides an extensible feature that provides a more comfortable and contorting fit by initially conformably fitting the diaper to the wearer and by sustaining this fit. While each extensible waist belt may be constructed from a number of extensible materials, the extensible waist belt preferably comprises a structural elastic-like film web. The structural elastic-like film (SELF) web exhibits an elastic-like behavior in the direction of elongation without the use of added elastic materials.

19 Claims, 14 Drawing Sheets

U.S. PATENT DOCUMENTS

| | | |
|---|---|---|
| 782,977 | 2/1905 | Madden . |
| 854,763 | 5/1907 | Scriven . |
| 1,507,949 | 9/1924 | Angier . |
| 1,582,842 | 4/1926 | Lorenz . |
| 2,007,047 | 7/1935 | Gibbs . |
| 2,158,929 | 5/1939 | Dunajeff . |
| 2,177,490 | 10/1939 | Kieffer . |
| 2,257,428 | 9/1941 | Ruegenberg . |
| 2,679,887 | 6/1954 | Doyle et al. . |
| 2,896,692 | 7/1959 | Villoresi . |
| 2,901,951 | 9/1959 | Hochfeld . |
| 2,974,716 | 3/1961 | Fourness . |
| 3,151,947 | 10/1964 | Hastings . |
| 3,236,718 | 2/1966 | Chohn et al. . |
| 3,313,080 | 4/1967 | Gewiss . |
| 3,351,441 | 11/1967 | Gewiss . |
| 3,362,118 | 1/1968 | Brunner . |
| 3,550,423 | 12/1970 | Gewiss . |
| 3,599,640 | 8/1971 | Larson . |
| 3,726,408 | 4/1973 | Gewiss . |
| 3,817,827 | 6/1974 | Benz . |
| 3,828,784 | 8/1974 | Zoephel . |
| 3,843,761 | 10/1974 | Bierenbaum et al. . |
| 3,860,003 | 1/1975 | Buell . |
| 3,880,966 | 4/1975 | Zimmerman et al. . |
| 3,894,352 | 7/1975 | Hooker . |
| 3,929,135 | 12/1975 | Thompson . |
| 3,969,473 | 7/1976 | Meek . |
| 3,975,455 | 8/1976 | Falender et al. . |
| 3,992,162 | 11/1976 | Gewiss . |
| 4,024,867 | 5/1977 | Mesek . |
| 4,031,568 | 6/1977 | Huff . |
| 4,036,233 | 7/1977 | Kozak . |
| 4,041,949 | 8/1977 | Kozak . |
| 4,051,854 | 10/1977 | Aaron . |
| 4,082,877 | 4/1978 | Shadle . |
| 4,104,430 | 8/1978 | Fenton . |
| 4,110,391 | 8/1978 | Berzen et al. . |
| 4,153,664 | 5/1979 | Sabee . |
| 4,205,679 | 6/1980 | Repke et al. . |
| 4,321,924 | 3/1982 | Ahr . |
| 4,323,070 | 4/1982 | Ternstrom et al. . |
| 4,324,246 | 4/1982 | Mullane et al. . |
| 4,342,314 | 8/1982 | Radel et al. . |
| 4,425,130 | 1/1984 | DesMarais . |
| 4,463,045 | 7/1984 | Ahr et al. . |
| 4,486,192 | 12/1984 | Sigl . |
| 4,554,121 | 11/1985 | Kramers . |
| 4,568,344 | 2/1986 | Suzuki et al. . |
| 4,576,599 | 3/1986 | Lipner . |
| 4,589,876 | 5/1986 | VanTilburg . |
| 4,609,518 | 9/1986 | Curro et al. . |
| 4,610,682 | 9/1986 | Kopp . |
| 4,617,241 | 10/1986 | Mueller . |
| 4,640,859 | 2/1987 | Hansen et al. . |
| 4,662,874 | 5/1987 | Korpman . |
| 4,699,620 | 10/1987 | Bernardin . |
| 4,701,174 | 10/1987 | Johnson . |
| 4,704,115 | 11/1987 | Buell . |
| 4,719,261 | 1/1988 | Bunnelle et al. . |
| 4,731,066 | 3/1988 | Korpman . |
| 4,743,241 | 5/1988 | Igaue et al. . |
| 4,756,709 | 7/1988 | Stevens . |
| 4,771,483 | 9/1988 | Hooreman et al. . |
| 4,780,344 | 10/1988 | Hoberman . |
| 4,834,741 | 5/1989 | Sabee . |
| 4,847,134 | 7/1989 | Fahrenbkrug et al. . |
| 4,892,536 | 1/1990 | DesMarais et al. . |
| 4,906,243 | 3/1990 | Dravland . |
| 4,935,021 | 6/1990 | Huffman et al. . |
| 4,938,753 | 7/1990 | Van Gompel et al. . |
| 4,950,264 | 8/1990 | Osborn . |
| 4,968,313 | 11/1990 | Sabee . |
| 4,977,011 | 12/1990 | Smith . |
| 4,995,873 | 2/1991 | Knight . |
| 5,006,394 | 4/1991 | Baird . |
| 5,008,140 | 4/1991 | Schmertz . |
| 5,028,474 | 7/1991 | Czaplicki . |
| 5,034,078 | 7/1991 | Hodgson, Jr. et al. . |
| 5,098,755 | 3/1992 | Tanquary . |
| 5,143,679 | 9/1992 | Weber et al. . |
| 5,151,092 | 9/1992 | Buell et al. .......................... 604/385.2 |
| 5,187,817 | 2/1993 | Zolner . |
| 5,196,000 | 3/1993 | Clear et al. . |
| 5,202,173 | 4/1993 | Wu et al. . |
| 5,204,997 | 4/1993 | Suzuki et al. . |
| 5,205,650 | 4/1993 | Rasmussen . |
| 5,234,423 | 8/1993 | Alemany et al. . |
| 5,236,430 | 8/1993 | Bridges . |
| 5,254,111 | 10/1993 | Cancio et al. . |
| 5,296,184 | 3/1994 | Wu et al. . |
| 5,358,500 | 10/1994 | LaVon et al. . |
| 5,370,634 | 12/1994 | Ando et al. . |
| 5,518,801 | 5/1996 | Chappell et al. . |

ABSORBENT ARTICLE WITH STRUCTURAL ELASTIC-LIKE FILM WEB WAIST BELT

This is a division of application Ser. No. 08/333,921, filed on Nov. 7, 1994, now abandoned, which is a continuation-in-part of application Ser. No. 08/155,406 filed Nov. 19, 1993, now abandoned.

FIELD OF THE INVENTION

The present invention relates to absorbent articles such as diapers, incontinent briefs, training pants, and the like, and more particularly, to absorbent articles having an extensible waist feature providing dynamic fit about the wearer as well as improved containment characteristics of the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractible Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the wearer, certain commercially available absorbent articles have been provided with elastic features. An example of a disposable diaper with elastic side panels is disclosed in U.S. Pat. No. 5,151,092, entitled "Absorbent Article With Dynamic Elastic Waist Feature Having Predisposed Flexural Hinge" issued to Buell, Clear, and Falcone on Sep. 22, 1992. However, elastics are costly and require a certain degree of manipulation and handling during assembly. Further, while elastics do provide a degree of stretch for the absorbent article, the components of the absorbent article to which the elastics are attached are typically not elastic such that the elastics must be prestretched prior to being secured to the absorbent article or the inelastic components must be subjected to mechanical stretching (e.g., ring rolling) to enable the added elastic to be effective. Otherwise, the added elastic is restrained by the inelastic components.

Therefore, it is an object of the present invention to provide a relatively low cost, easy to manufacture, absorbent article having sustained dynamic fit about the wearer during use.

It is a further object of the present invention to provide an absorbent article having a unique waist feature, without the use of elastic, that provides sustained dynamic fit and improved resistance to leakage during use due to the conformability of the materials forming the waist feature by virtue of their readily extensible nature.

It is a still further object of the present invention to provide a waist feature on an absorbent article that exhibits an "elastic-like" behavior in the direction of applied force or elongation without the use of additional elastic material.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants, feminine hygiene garments and the like, that have a unique waist feature that improves the dynamic fit as well as the containment characteristics of the absorbent article. Such absorbent articles comprise a chassis assembly preferably comprising a liquid pervious topsheet, a liquid impervious backsheet, and an absorbent core positioned between the topsheet and the backsheet; an extensible waist belt; and a closure system for maintaining the absorbent article on the wearer. The absorbent core has side edges and waist edges.

In an especially preferred embodiment of the present invention, the absorbent article has a T-shape comprising a chassis assembly and an extensible waist belt disposed in the second waist region. The extensible waist belt provides an extensible feature that provides a more comfortable and contorting fit by initially conformably fitting the diaper to the wearer and by sustaining this fit. The extensible waist belt further develops and maintains wearing forces (tensions) that enhance the tensions developed and maintained by the closure system. The extensible waist belt further provides more effective application of the diaper. While each extensible waist belt may be constructed from a number of extensible materials, the extensible waist belt preferably comprises a structural elastic-like film web.

The structural elastic-like film (SELF) web exhibits an elastic-like behavior in the direction of elongation without the use of added elastic materials. The SELF web may exhibit an elongation and recovery with a definite and sudden increase in the force resisting elongation where this definite and sudden increase in resistive force restricts further elongation against relatively small elongation forces. The definite and sudden increase in the force resisting elongation is referred to as a "force wall". As used herein, the term "force wall" refers to the behavior of the resistive force of a SELF web material during elongation wherein at some point in the elongation, distinct from the untensioned or starting point, the force resisting the applied elongation suddenly increases. After reaching the force wall, additional elongation of the SELF web material is only accomplished via an increase in the elongation force to overcome the higher resistive force of the SELF web.

The SELF web of the present invention includes a strainable network having at least two distinct regions comprised of the same material composition. The first region is oriented substantially parallel to an axis of elongation such that it will undergo a molecular-level deformation in response to an applied axial elongation in a direction substantially parallel to the elongation axis before a substantial portion of the second region undergoes any substantial molecular-level deformation. As used herein, the term "substantially parallel" refers to an orientation between two axes whereby the subtended angle formed by the two axes or an extension of the two axes is less than 45°. In the case of a curvilinear element it may be more convenient to use a linear axis which represents an average of the curvilinear element. The second regions initially undergo a substantially geometric deformation in response to an applied elongation in a direction substantially parallel to the axis.

In a particularly preferred embodiment, the second region of the SELF web is comprised of a plurality of raised rib-like elements. As used herein, the term "rib-like element" refers to an embossment, debossment or combination thereof which has a major axis and a minor axis. Preferably, the major axis is at least as long as the minor axis. The major axes of the rib-like elements are preferably oriented substantially perpendicular to the axis of applied elongation. The major axis and the minor axis of the rib-like elements may each be linear, curvilinear or a combination of linear and curvilinear. As used herein, the term "substantially perpendicular" refers to an orientation between two axes whereby the subtended angle formed by the two axes or an extension of the two axes is greater than 45°. In the case of a curvilinear element it may be more convenient to use a linear axis which represents an average of the curvilinear element.

The rib-like elements allow the second region to undergo a substantially "geometric deformation" which results in significantly less resistive forces to an applied elongation than that exhibited by the "molecular-level deformation" of the first region. As used herein, the term "molecular-level deformation" refers to deformation which occurs on a molecular level and is not discernible to the normal naked eye. That is, even though one may be able to discern the effect of a molecular-level deformation, e.g., elongation of the SELF web, one is not able to discern the deformation which allows or causes it to happen. This is in contrast to the term "geometric deformation". As used herein, the term "geometric deformation" refers to deformations of the SELF web which are generally discernible to the normal naked eye when the SELF web or articles embodying the SELF web are subjected to an applied elongation. Types of geometric deformation include, but are not limited to bending, unfolding, and rotating.

The SELF web preferably exhibits at least two significantly different stages of resistive force to an applied elongation along at least one axis when subjected to an applied elongation in a direction parallel to the axis. The SELF web includes a strainable network having at least two distinct regions. One of the regions is configured such that it will exhibit resistive forces in response to an applied axial elongation in a direction parallel to the axis before a substantial portion of the other region develops significant resistive forces to the applied elongation. At least one of the regions has a surface-pathlength which is greater than that of the other region as measured substantially parallel to the axis while the material is in an untensioned condition. The region exhibiting the longer surface-pathlength includes one or more rib-like elements which extend beyond the plane of the other region. The SELF web exhibits first resistive forces to the applied elongation until the elongation of the web is sufficient to cause a substantial portion of the region having the longer surface-pathlength to enter the axis of applied elongation, (i.e., become essentially coplanar with the axis of applied elongation), whereupon the SELF web exhibits second resistive forces to further elongation. The total resistive force to elongation is higher than the first resistive force to elongation provided by the first region.

Preferably, the first region has a first surface-pathlength, L1, as measured substantially parallel to the predetermined axis while the SELF web is in an untensioned condition. The second region has a second surface-pathlength, L2, as measured substantially parallel to the predetermined axis while the SELF web is in an untensioned condition. The first surface-pathlength, L1, is less than the second surface-pathlength, L2. The first region preferably has an elastic modulus E1. The first region has a cross-sectional area A1. The first region produces by itself a resistive force, P1, due to molecular-level deformation in response to an applied axial elongation, D. The second region produces a resistive force, P2, due to geometric deformation in response to the applied axial elongation, D. The second region preferably has an elastic modulus E2, and a cross-sectional area A2. The resistive force, P1, is significantly greater than the resistive force, P2, so long as (L1+D) is less than L2.

Preferably, while (L1+D) is less than L2 the first region provides an initial resistive force to the applied axial elongation, D, substantially satisfying the equation (A1×E1×D)/L1. When (L1+D) is greater than L2 the first and second regions provide a combined total resistive force, PT, to the applied axial elongation, D, satisfying the equation:

$$PT = \frac{(A1 \times E1 \times D)}{L1} + \frac{(A2 \times E2 \times |L1 + D - L2|)}{L2}$$

In a preferred embodiment, the SELF web exhibits a Poisson lateral contraction effect less than about 0.4 at 20% elongation as measured perpendicular to the axis of elongation. As used herein, the term "Poisson lateral contraction effect" describes the lateral contraction behavior of a material which is being subjected to an applied elongation. Preferably, the SELF web exhibits a Poisson lateral contraction effect less than about 0.4 at 60% elongation as measured perpendicular to the axis of elongation.

The surface-pathlength of the second region is at least about 15% greater than that of the first region as measured parallel to the axis of elongation while the SELF web is in an untensioned condition. Preferably, the surface pathlength of the second region is at least about 30% greater than that of the first region as measured parallel to the axis of elongation while the SELF web is in an untensioned condition.

Preferably, the absorbent article has an end edge in a first waist region and an end edge in a second waist region. Preferably, one of the waist edges of the absorbent core is spaced from the adjacent end edge of the absorbent article in the first waist region by a distance A. The other waist edge of the absorbent core is spaced from the adjacent end edge of the absorbent article in the second waist region by a distance of at least 2A.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, training pants, feminine hygiene garments, and the like.

Figure 1:
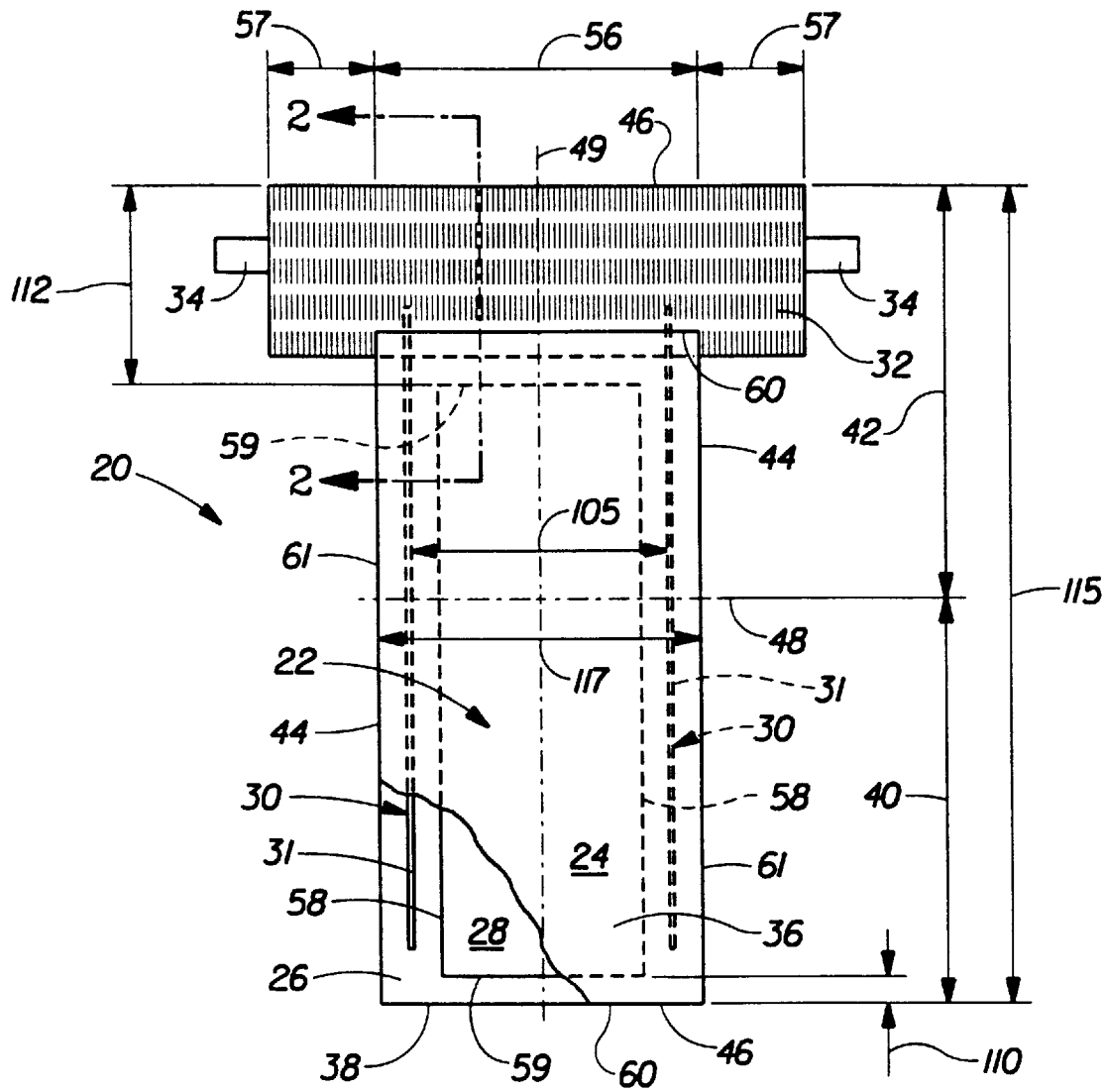
FIG. 1 is a plan view of a disposable diaper embodiment of the present invention having portions cut-away to reveal underlying structure, the inner surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which contacts the wearer, the inner surface, facing the viewer. As shown in FIG. 1, the diaper 20 has a generally "T-shape" and comprises (a) a chassis assembly 22 preferably comprising: a liquid pervious topsheet 24, a liquid impervious backsheet 26 joined with the topsheet 24, an absorbent core 28 positioned between the topsheet 24 and the backsheet 26, and elasticized leg cuffs 30; (b) an extensible waist belt 32; and (c) a closure system for fastening the diaper on the wearer comprising a pair of tape tabs 34.

The diaper 20 is shown in FIG. 1 to have an inner surface 36 (facing the viewer in FIG. 1), an outer surface 38 opposed to the inner surface 36, a first waist region 40, a second waist region 42 opposed to the first waist region 40, and a periphery which is defined by the outer edges of the diaper 20 in which the longitudinal edges are designated 44 and the end edges are designated 46. (While the skilled artisan will recognize that a diaper is usually described in terms of having a pair of waist regions and a crotch region between the waist regions; in this application, for simplicity of terminology, the diaper 20 is described as having only waist regions, each of the waist regions including a portion of the diaper which would typically be designated as part of the crotch region). The inner surface 36 of the diaper 20 comprises that portion of the diaper 20 which is positioned adjacent to the wearer's body during use (i.e., the inner surface 36 generally is formed by at least a portion of the topsheet 24 and other components joined to the topsheet 24). The outer surface 38 comprises that portion of the diaper 20 which is positioned away from the wearer's body (i.e., the outer surface 38 generally is formed by at least a portion of the backsheet 26 and other components joined to the backsheet 26). The first waist region 40 and the second waist region 42 extend, respectively, from the end edges 46 of the periphery to the lateral centerline 48 of the diaper 20. (The lateral direction (x direction or width) is defined as the direction parallel to the lateral centerline 48 of the diaper 20; the longitudinal direction (y direction or length) being defined as the direction parallel to the longitudinal centerline 49; and the axial direction (Z direction or thickness) being defined as the direction extending through the thickness of the diaper 20.)

FIG. 1 shows a preferred embodiment of the chassis assembly 22 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery of the diaper. The periphery defines the outer perimeter or, in other words, the edges of the diaper 20. The periphery comprises the longitudinal edges 44 and the end edges 46.

Figure 2:
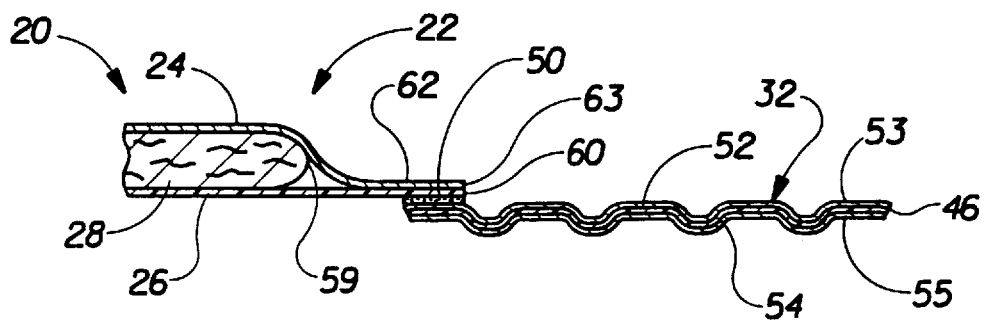
FIG. 2 is a sectional view of the disposable diaper shown in FIG. 1 taken along section line 2—2 of FIG. 1.

FIG. 2 is a cross-sectional view of the diaper 20 taken along section line 2—2 of FIG. 1 in the second waist region 42. FIG. 2 shows the construction of the chassis assembly 22, the waist belt 32, and the joining of the waist belt 32 with the chassis assembly 22. The chassis assembly 22 comprises the topsheet 24, the backsheet 26, and the absorbent core 28 (generally shown in FIG. 2). The topsheet 24 and the backsheet 26 preferably extend longitudinally outwardly beyond the waist edge 59 of the absorbent core 28 to form an end flap 62; the lateral edge 60 of the chassis assembly 22 being formed at the distal edge 63 of the end flap 62 by the edge of the topsheet 24 and the backsheet 26. The waist belt 32 is joined to the end flap 62 of the chassis assembly 22 adjacent the lateral edge 60. As shown in FIG. 2, the waist belt 32 is preferably directly joined to the backsheet 26 by a belt attachment element 50. The waist belt 32 is shown in FIG. 2 to comprise a structural elastic-like film (SELF) web 52 (as described hereinafter) preferably comprised of a laminate of two or more layers, in the embodiment shown in FIG. 2 comprising three layers: an inner layer 53, an outer layer 55, and a support layer 54 between the inner layer 53 and the outer layer 55. The inner layer 53 is the layer joined to the backsheet 26 by the belt attachment element 50.

The chassis assembly 22 of the diaper 20 is shown in FIG. 1 as comprising the main body (chassis) of the diaper 20. The chassis assembly 22 comprises at least an absorbent core 28, preferably an outer covering layer comprising the topsheet 24 and the backsheet 26, and more preferably elasticized leg cuffs 30. The chassis assembly 22 has a pair of leg edges 61 which typically form a portion of the longitudinal edges 44 of the diaper and a pair of lateral edges 60. In the embodiment shown in FIG. 1, the extensible waist belt 32 is joined to one of the lateral edges while the other lateral edge forms one of the end edges 46 of the diaper 20. Thus, the chassis assembly 22 comprises the main structure of the diaper with other features added to form the composite diaper structure. An exemplary example of a chassis assembly of the present invention is described in U.S. Pat. No. 3,860,003 issued to Kenneth B. Buell on Jan. 14, 1975, which patent is incorporated herein by reference.

The diaper 20 as shown in FIG. 1, has a generally "T-shape". The waist edge 59 of the absorbent core 28 in the first waist region 40 is spaced from the adjacent end edge 46 of the diaper 20 in the first waist region by a distance A, indicated as 110 in FIG. 1. Preferably, the distance A is in the range of from about 1.5 centimeters to 8.0 centimeters, more preferably from about 1.5 centimeters to 5.0 centimeters, and most preferably is about 2.0 centimeters. The other waist edge 59 of the absorbent core 28 in the second waist region 42 is spaced from the adjacent end edge 46 of the diaper 20 in the second waist region by a distance indicated as 112. Distance 112 is preferably at least 2A, more preferably at least 3A, and most preferably is about 4A.

The distance 112, the distance between the waist edge 59 of the absorbent core in the second waist region 42 and the adjacent end edge 46 of the diaper in the second waist region is not necessarily dependent upon or defined by the dimension A, (i.e,. the spacing of the waist edge of the absorbent core is the first waist region from the adjacent end edge of the diaper is the first waist region). The distance 112 is preferably at least 6.0 centimeters, more preferably at least 7.0 centimeters, and most preferably at least 8.0 centimeters. A particularly preferred embodiment of a disposable diaper 20 has a distance 112 of about 9.0 centimeters.

Referring now to FIG. 1, the chassis 22 has a length 115 which extends between the end edges 46 located in the first waist region 40 and the second waist region 42, respectively. The chassis 22 has a crotch width 117, which is measured at the narrowest portion of the chassis between the leg edges 61. The boundaries of the crotch width 117 and the crotch length 115 define the main panel of the chassis. The main panel of the chassis is that portion of the chassis which typically contains a substantial portion, and frequently, the entire absorbent core.

The absorbent core 28 may be any absorbent means which is capable of absorbing and retaining liquids such as urine and other certain body exudates. The absorbent core 28 has a garment surface, a body surface, side edges 58, and waist edges 59. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. A preferred embodiment of the diaper has a rectangular-shape absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany and Berg on May 30, 1989, also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these references are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids which have passed through the topsheet and are contained in the absorbent core 28 (i.e., to prevent rewet). If the topsheet is made of a hydrophobic material, at least the upper surface thereof is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the material with the surfactant and immersing the material in the surfactant. A more detailed discussion of such a treatment and hydrophilicity is contained in U.S. Pat. No. 4,988,344 entitled "Absorbent Articles With Multiple Layer Absorbent Layers" issued to Reising, et al. on Jan. 29, 1991.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The chassis assembly 22 preferably further comprises elasticized leg cuffs 30 for providing improved containment of liquids and other body exudates. Each elasticized leg cuff 30 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractible Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 30 may be configured so as to be similar to any of the leg bands, side flaps, barrier cuffs, or elastic cuffs described above, it is preferred that each elasticized leg cuff 30 comprise the gasketing cuff such as described in the above-referenced U.S. Pat. No. 3,860,003.

Each elasticized leg cuff 30 is shown in FIG. 1 as comprising one elastic element 31. In some embodiments it may be desirable to have each elasticized leg cuff 30 comprise a plurality of elastic elements 31. The elastic elements 31 extend is beyond the waist edge 59 of the absorbent core 28 and into the extensible waist belt 32. Prior to use, the opposite innermost ones of the elastic elements 31 positioned on opposite sides of the absorbent core are substantially linear and are substantially parallel to one another throughout their length. Prior to use, the elastic elements 31 are also aligned substantially parallel to both the side edges 58 of the absorbent core 28 and to the leg edges 61 of the chassis assembly 22 throughout their length.

The dimension between opposite innermost ones of the elastic elements is substantially uniform throughout their length prior to use. The dimension between opposite innermost ones of the elastic elements is indicated as 105 in FIG. 1. The dimension between opposite innermost ones of elastic elements is measured across the absorbent core 28 parallel to the lateral centerline 48 of the diaper. During use, the extensible waist belt 32 extends or is extended in the lateral direction as it is worn by or positioned onto the wearer. As the waist belt 32 extends in the lateral direction during use, the dimension between opposite innermost ones of the elastic elements positioned within the extensible waist belt increases, while the remaining portion of opposite innermost ones of the elastic elements remains substantially unchanged. Therefore, during use, the dimension between opposite innermost ones of the elastic elements positioned within the extensible waist belt is greater than the dimension between the remaining portion of opposite innermost ones of the elastic elements, e.g., the portion of the elastic elements positioned adjacent the side edges of the absorbent core.

The diaper 20 further comprises an extensible waist belt 32 that provides improved fit and containment. The extensible waist belt 32 at least extends laterally outwardly from each leg edge 61 of the chassis assembly 22 and preferably longitudinally outwardly from one of the lateral edges of the chassis assembly 22. Thus, in the embodiment shown in FIG. 1, the extensible waist belt 32 comprises that portion of the diaper at least extending from the lateral edge 60 of the chassis assembly 22 in the second waist region 42 to the end edge 46 of the diaper 20 and is intended to be placed adjacent the wearer's waist. While a disposable diaper of the present invention can be constructed with an extensible waist belt 32 joined to each lateral edge 60 of the chassis assembly 22, the discussion regarding the extensible waist belt 32 will focus on diapers having a single extensible waist belt being constructed according to the present invention in order to form a "T-shaped" diaper. Further, while the waist belt or any of its constituent elements can be constructed as an extension of other elements of the diaper such as the backsheet 26 or the topsheet 24 or both (such as is shown in the above-referenced U.S. Pat. No. 3,860,003), the waist belt 32 will be described with respect to a preferred embodiment in which the waist belt is a separate element joined to the chassis assembly 22.

The waist belt 32 provides an extensible feature that provides a more comfortable and contorting fit by initially conformably fitting the diaper to the wearer and sustaining this fit throughout the time of wear well past when the diaper has been loaded with exudates since the extensible waist belt allows the sides of the diaper to expand and contract without the use of additional elastic materials. Further, the extensible waist belt develops and maintains wearing forces (tensions) that enhance the tensions developed and maintained by the closure system to maintain the diaper 20 on the wearer and that enhance the fit of the diaper about the waist of the wearer. The extensible waist belt further provides more effective application of the diaper 20 since even if the diaperer pulls one side (side panel) of the extensible waist belt farther than the other during application (asymmetrically), the diaper 20 will "self-adjust" during wear. While the diaper 20 of the present invention preferably has an extensible waist belt 32 disposed in the second waist region 42; alternatively, the diaper 20 may be provided with an extensible waist belt disposed in the first waist region 40 or one disposed in both the first waist region 40 and the second waist region 42.

As shown in FIG. 1, the waist belt 32 has a central waist panel 56 and a pair of side panels 57, one being disposed on each side of the central waist panel 56. The central waist panel 56 is that portion of the waist belt 32 between the leg edges 61 of the chassis assembly 22. Thus, the central waist panel 56 is coterminous or coextensive with the width of the chassis assembly 22 at the lateral edge 60. The side panels 57 extend laterally outwardly from the central waist panel 56 beyond the leg edges 61 of the chassis assembly 22. In order to provide the fit and containment benefits of the waist belt as discussed herein, at least the side panels 57 of the waist belt 32 must be extensible. In the preferred embodiment shown in FIG. 1, the central waist panel 56 as well as the side panels 57 are preferably extensible to provide a total waist feature which is conformable to the wearer to provide fit and containment benefits.

The waist belt 32 may take on a number of different sizes, shapes and configurations and may be constructed from a number of different materials. For example, the waist belt may be formed from one or more separate members, including portions of the chassis assembly 22, being joined together to form a coordinated entity; or, the waist belt 32, as shown in FIG. 1, may comprise a single piece of material. The waist belt may also have varying widths and lengths to provide fit to different ranges of wearers or for cost or containment reasons. Further, the shape of the waist belt may be varied considerably from having complex curves and angles to simply being rectangular in shape such as shown in FIG. 1. Examples of complex shapes useful for the shape of the waist belt are disclosed in U.S. patent application Ser. No. 08/044,562 entitled "Fitted Belt For Absorbent Garment" filed by New, et al. on Apr. 7, 1993 which application is incorporated herein by reference.

While the waist belt 32 may be constructed from a number of different extensible materials as are known in the art, the waist belt, for performance and cost reasons, is preferably constructed of a structural elastic-like film (SELF) web. The term "web" herein refers to a sheet-like material comprising a single layer of material or a laminate of two or more layers.

Figure 5:
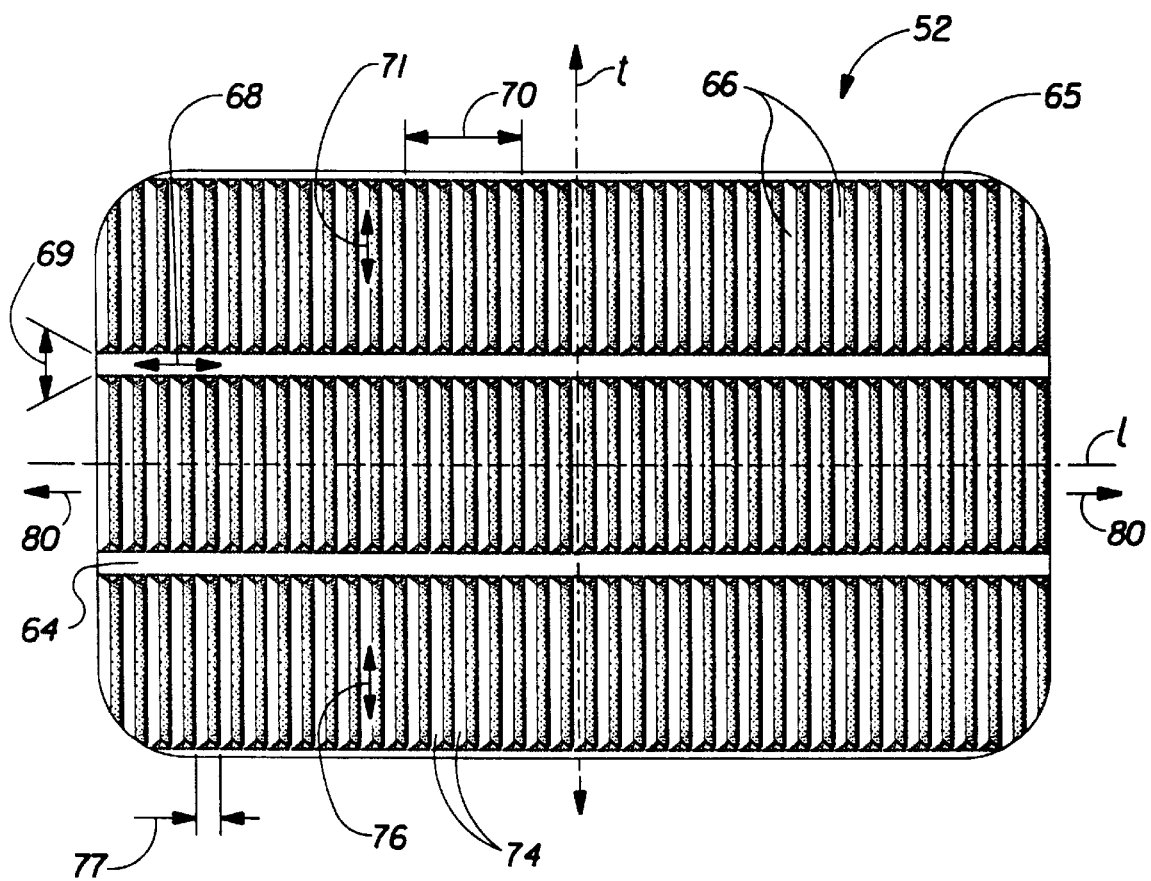
FIG. 5 is a plan view illustration of a preferred embodiment of a SELF web having a strainable network of the present invention with the deformations facing toward the viewer.

FIG. 5 shows a preferred embodiment of a SELF web 52 of the present invention constructed of a single layer of a formed polymeric material. The SELF web 52 is shown in its untensioned condition. The web has two centerlines, a longitudinal centerline, l, and a transverse or lateral centerline, t, which is generally perpendicular to the longitudinal centerline. The web is preferably comprised substantially of linear low density polyethylene (LLDPE) although it may also be comprised of other polyolefins such as polyethylenes including low density polyethylene (LDPE), ultra low density polyethylene (ULDPE), high density polyethylene (HDPE) or polypropylene and/or blends thereof of the above and other materials. Examples of other suitable polymeric materials include, but are not limited to, polyester, polyurethanes, compostable or biodegradable polymers, and breathable polymers.

Figure 5A:
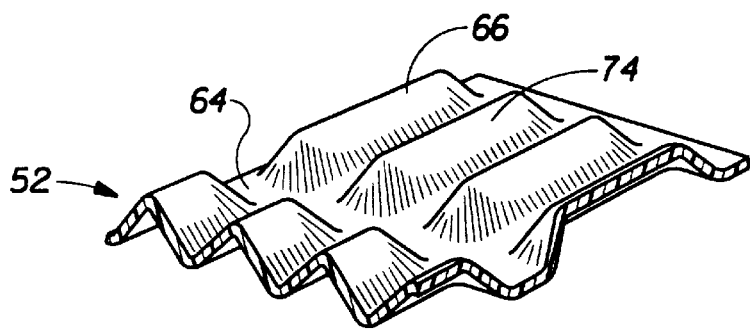
FIG. 5A is a segmented, perspective illustration of the SELF web of FIG. 5 in an untensioned condition.

Referring to FIGS. 5 and 5A, the SELF web includes a "strainable network" of distinct regions. As used herein, the term "strainable network" refers to an interconnected and interrelated group of regions which are able to be extended to some useful degree in a predetermined direction providing the SELF web with an elastic-like behavior in response to an applied and subsequently released elongation. The strainable network includes at least a first region 64 and a second region 66. The SELF web 52 includes a transitional region 65 which is at the interface between the first region 64 and the second region 66. The transitional region 65 will similarly exhibit complex combinations of behavior of both the first region and the second region. It is recognized that every embodiment of the present invention will have transitional regions, however, the present invention is largely defined by the behavior of the web material in the distinctive regions (e.g., first region 64 and second region 66). Therefore, the ensuing description of the present invention will be concerned with the behavior of the web material in the first regions and the second regions only since it is not significantly dependent upon the complex behavior of the web material in the transitional regions 65.

SELF web 52 has a first surface and an opposing second surface. In the preferred embodiment shown in FIGS. 5 and 5A, the strainable network includes a plurality of first regions 64 and a plurality of second regions 66. The first regions 64 have a first axis 68 and a second axis 69, wherein the first axis 68 is preferably longer than the second axis 69. The first axis 68 of the first region 64 is substantially parallel to the longitudinal axis of the SELF web 52 while the second axis 69 is substantially parallel to the transverse axis of the SELF web 52. Preferably, the second axis of the first region, (i.e., the width of the first region), is from about 0.01 inches to about 0.5 inches, and more preferably from about 0.03 inches to about 0.25 inches. The second regions 66 have a first axis 70 and a second axis 71. The first axis 70 is substantially parallel to the longitudinal axis of the SELF web 52, while the second axis 71 is substantially parallel to the transverse axis of the SELF web 52. Preferably, the second axis of the second region, (i.e., the width of the second region), is from about 0.01 inches to about 2.0 inches, and more preferably, from about 0.125 inches to about 1.0 inches. In the preferred embodiment of FIG. 5, the first regions 64 and the second regions 66 are substantially linear, extending continuously in a direction substantially parallel to the longitudinal axis of the SELF web 52.

The first region 64 has an elastic modulus E1 and a cross-sectional area A1. The second region 66 has an elastic modulus E2 and a cross-sectional area A2.

In the illustrated embodiment, a portion of the SELF web 52 has been "formed" such that the SELF web 52 exhibits a resistive force along an axis, which in the case of the illustrated embodiment is substantially parallel to the longitudinal axis of the SELF web, when subjected to an applied axial elongation in a direction substantially parallel to the longitudinal axis. As used herein, the term "formed" refers to the creation of a desired structure or geometry upon the SELF web that will substantially retain the desired structure or geometry when it is not subjected to any externally applied elongations or forces. A SELF web of the present invention is comprised of at least a first region and a second region, wherein the first region is visually distinct from the second region. As used herein, the term "visually distinct" refers to features of the SELF web material which are readily discernible to the normal naked eye when the SELF web material or objects embodying these SELF web material are subjected to normal use. Preferably, the first region has a "surface-pathlength" less than that of the second region, as measured parallel to a predetermined axis when the material is in an untensioned state. As used herein, the term "surface-pathlength" refers to a measurement along the topographic surface of the region in question in a direction parallel to an axis. The method for determining the surface-pathlength of the respective regions can be found in the Test Methods section set forth in subsequent portions of the present specification.

Methods for forming SELF web materials include, but are not limited to, embossing by mating plates or rolls, thermoforming, high pressure hydraulic forming, or casting. While the entire portion of the SELF web 52 has been subjected to a forming operation, the present invention may also be practiced by subjecting to formation only a portion thereof, e.g., a portion of a diaper backsheet.

In the preferred embodiment shown in FIGS. 5 and 5A, the first regions 64 are substantially planar. That is, the material within the first region 64 is in substantially the same condition before and after the formation step undergone by the SELF web 52. The second regions 66 include a plurality of raised rib-like elements 74. The rib-like elements 74 may be embossed, debossed or a combination thereof The rib-like elements 74 have a first or major axis 76 which is substantially parallel to the transverse axis of the SELF web 52 and a second or minor axis 77 which is substantially parallel to the longitudinal axis of the SELF web 52. The first axis 76 of the rib-like elements 74 is at least equal to, and preferably longer than the second axis 77. Preferably, the ratio of lengths of the first axis 76 to the second axis 77 is at least about 1:1, or greater, and more preferably at least about 2:1 or greater.

The rib-like elements 74 in the second region 66 may be separated from one another by unformed areas, essentially unembossed or debossed, or simply formed as spacing areas. Preferably, the rib-like elements 74 are adjacent one another and are separated by an unformed area of less than 0.10 inches as measured perpendicular to the major axis 76 of the rib-like element 74, and more preferably, the rib-like element 74 are contiguous having no unformed areas between them.

The first region 64 and the second region 66 each have a "projected pathlength". As used herein, the term "projected pathlength" refers to length of a shadow of a region that would be thrown by parallel light. The projected pathlength of the first region 64 and the projected pathlength of the second region 66 are equal to one another.

The first region 64 has a surface-pathlength, L1, less than the surface-pathlength, L2, of the second region 66 as measured topographically in a direction parallel to the longitudinal axis of the SELF web while the SELF web is in an untensioned condition. Preferably, the surface-pathlength of the second region 66 is at least about 15% greater than that of the first region 64, more preferably at least about 30% greater than that of the first region, and most preferably at least about 70% greater than that of the first region. In general, the greater the surface-pathlength of the second region, the greater will be the elongation of the SELF web before encountering the force wall.

What makes the SELF web particularly well suited for use as the waist belt 32 is that it exhibits a modified "Poisson lateral contraction effect" substantially less than that of an otherwise identical unformed base web of similar material composition. As used herein, the term "Poisson lateral contraction effect" describes the lateral contraction behavior of a material which is being subjected to an applied elongation. The method for determining the Poisson lateral contraction effect of a material can be found in the Test Methods section set forth in subsequent portions of the present specification. Preferably, the Poisson lateral contraction effect of the SELF web of the present invention is less than about 0.4 when the SELF web is subjected to about 20% elongation. Preferably, the SELF web exhibits a Poisson lateral contraction effect less than about 0.4 when the SELF web is subjected to about 40, 50 or even 60% elongation. The Poisson lateral contraction effect of the webs of the present invention is determined by the amount of the web material which is occupied by the first and second regions, respectively. As the area of the SELF web material occupied by the first region increases, the Poisson lateral contraction effect also increases. Conversely, as the area of the SELF web material occupied by the second region increases the Poisson lateral contraction effect decreases.

Preferably, the percent area of the SELF web material occupied by the first region is from about 2% to about 90%, and more preferably from about 5% to about 50%.

Web materials of the prior art which have at least one layer of an elastomeric material will generally have a large Poisson lateral contraction effect, i.e., they will "neck down" as they elongate in response to an applied force. SELF web materials of the present invention can be designed to moderate if not substantially eliminate the Poisson lateral contraction effect.

For the SELF web 52, the direction of applied axial elongation, D, indicated by arrows 80 in FIG. 5, is substantially perpendicular to the first axis 76 of the rib-like elements 74. The rib-like elements 74 are able to unbend or geometrically deform in a direction substantially perpendicular to their first axis 76 to allow extension in the SELF web 52.

Figure 6:
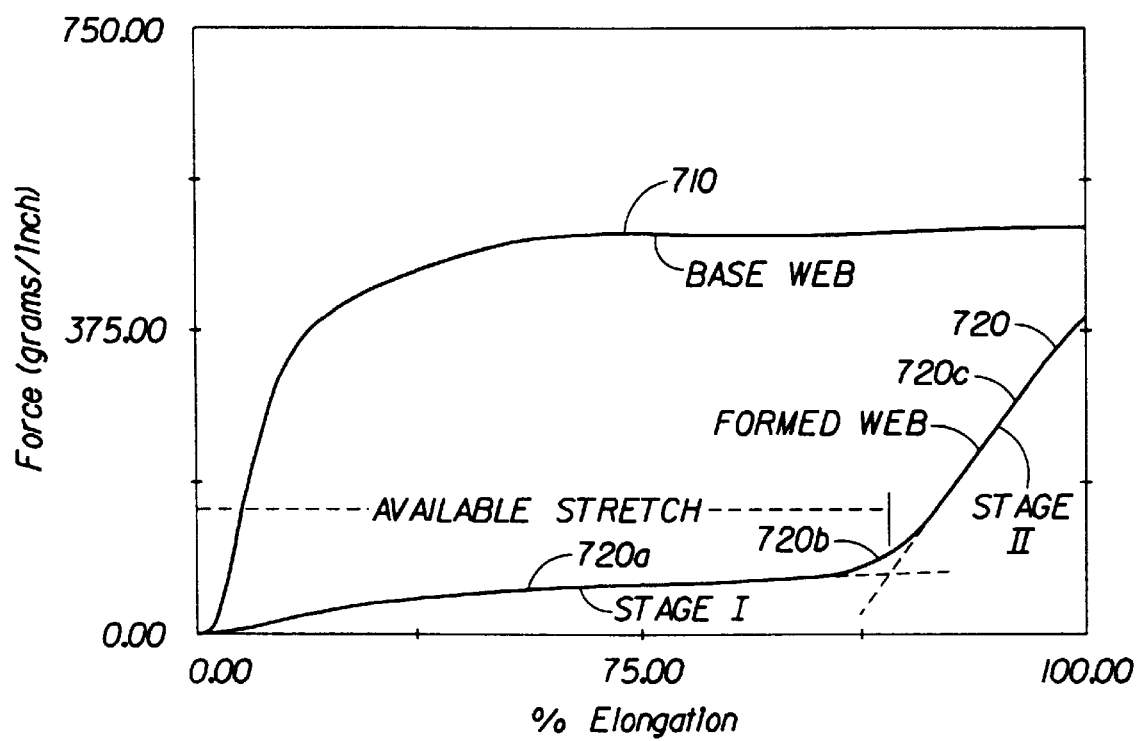
FIG. 6 is a graph of the resistive force versus percent elongation comparing the behavior of the SELF web of the present invention as shown in FIG. 5, with an otherwise identical, planar, base polymeric web material.

In FIG. 6 there is shown a graph of the resistive force-elongation curve 720 of a formed polymeric SELF web of the present invention along with a curve 710 of a base web material, i.e., not including first and second regions, of similar material composition. Specifically, the samples are polymeric web materials comprised substantially of linear low density polyethylene, approximately 0.001 inches thick, marketed under the designation Sample 1401 available from Clopay Corporation of Cincinnati, Ohio. The method for generating the resistive force-elongation curves can be found in the Test Methods section set forth in subsequent portions of the present specification. Referring now to the force-elongation curve 720, there is an initial substantially linear, lower force versus elongation stage I designated 720*a*, a transition zone designated 720*b* which indicates the encounter of the force wall, and a substantially linear stage II designated 720*c* which displays substantially higher force versus elongation behavior.

As seen in FIG. 6, a SELF web having a strainable network exhibits different elongation behavior in the two stages when subjected to an applied elongation in a direction parallel to the longitudinal axis of the SELF web. The resistive force exerted by the SELF web to the applied elongation is significantly less in stage I region (720*a*) versus the stage II region (720*c*) of curve 720. Furthermore, the resistive force exerted by the SELF web to the applied elongation as depicted in stage I (720*a*) of curve 720 is significantly less than the resistive force exerted by the base web as depicted in curve 710 within the limits of elongation of stage I. As the SELF web is subjected to further applied elongation and enters stage II (720*c*) the resistive force exerted by the SELF web increases and approaches the resistive force exerted by the base web. The resistive force to the applied elongation for the stage I region (720*a*) of the SELF web is provided by the molecular-level deformation of the first region of the SELF web and the geometric deformation of the second region of the SELF web. This is in contrast to the resistive force to an applied elongation that is provided by the base web, depicted in curve 710 of FIG. 6, which results from molecular-level deformation of the entire web. Web materials of the present invention can be designed to yield virtually any resistive force in stage I which is less than that of the base web material by adjusting the percentage of the web surface which is comprised of the first and second regions, respectively. The force-elongation behavior of stage I can be controlled by adjusting the width, cross-sectional area, and the spacing of the first region and the composition of the base web.

Figure 5B:
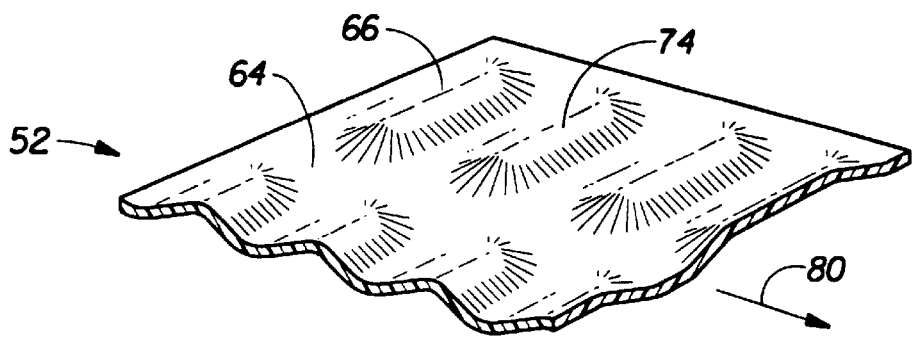
FIG. 5B is a segmented, perspective illustration of the SELF web of FIG. 5 in a tensioned condition corresponding to stage I on the force-elongation curve depicted in FIG. 6.
Figure 5C:
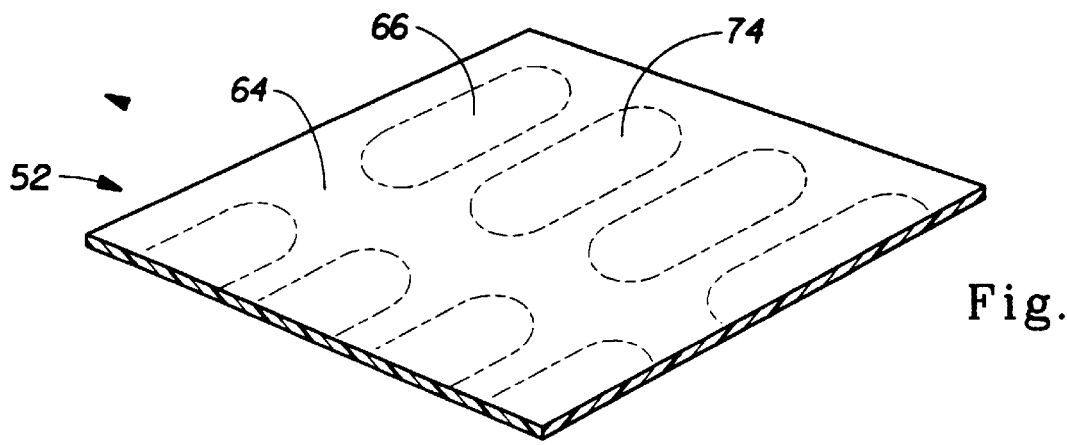
FIG. 5C is a segmented perspective illustration of the SELF web of FIG. 5 in a tensioned condition corresponding to stage II on the force-elongation curve depicted in FIG. 6.

Referring now to FIG. 5B, as the SELF web is subjected to an applied axial elongation, D, indicated by arrows 80 in FIG. 5, the first region 64 having the shorter surface-pathlength, L1, provides most of the initial resistive force, P1, as a result of molecular-level deformation, to the applied elongation which corresponds to stage I. While in stage I, the rib-like elements 74 in the second region 66 are experiencing geometric deformation, or unbending, and offer minimal resistance to the applied elongation. In the transition zone (720*b*) between stages I and II, the rib-like elements 74 are becoming aligned with the applied elongation. That is, the second region is exhibiting a change from geometric deformation to molecular-level deformation. This is the onset of the force wall. In stage II, as seen in FIG. 5C, the rib-like elements 74 in the second region 66 have become substantially aligned with the axis of applied elongation (i.e., the second region has reached its limit of geometric deformation) and begin to resist further elongation via molecular-level deformation. The second region 66 now contributes, as a result of molecular-level deformation, a second resistive force, P2, to further applied elongation. The resistive forces to elongation depicted in stage II by both the molecular-level deformation of the first region 64 and the molecular-level deformation of the second region 66 provide a total resistive force, PT, which is greater than the resistive force depicted in stage I which is provided by the molecular-level deformation of the first region 64 and the geometric deformation of the second region 66. Accordingly, the slope of the force-elongation curve in stage II is significantly greater than the slope of the force-elongation curve in stage I.

The resistive force P1 is substantially greater than the resistive force P2 when (L1+D) is less than L2. While (L1+D) is less than L2 the first region 64 provides an initial resistive force, P1, generally satisfying the equation:

$$P1 = \frac{(A1 \times E1 \times D)}{L1}$$

When (L1+D) is greater than L2 the first and second regions provide a combined total resistive force, PT, to the applied elongation D, generally satisfying the equation:

$$PT = \frac{(A1 \times E1 \times D)}{L1} + \frac{(A2 \times E2 \times |L1 + D - L2|)}{L2}$$

The maximum elongation occurring while in stage I is referred to as the "available stretch" of the SELF web. The available stretch corresponds to the distance over which the second region experiences geometric deformation. The available stretch can be effectively determined by inspection of the force-elongation curve 720 as shown in FIG. 6. The approximate point at which there is an inflection in the transition zone between stage I and stage II is the percent elongation point of "available stretch". The range of available stretch can be varied from about 10% to 100% or more; this range of elastic-like response is often found to be of interest in disposable absorbent articles, and can be largely controlled by the extent to which surface-pathlength L2 in the second region 66 exceeds surface-pathlength L1 in the first region 64 and the composition of the base film. The term "available stretch" is not intended to imply a limit to the elongation which the SELF web of the present invention may be subjected to as there are applications where elongation beyond the available stretch is desired.

Figure 7:
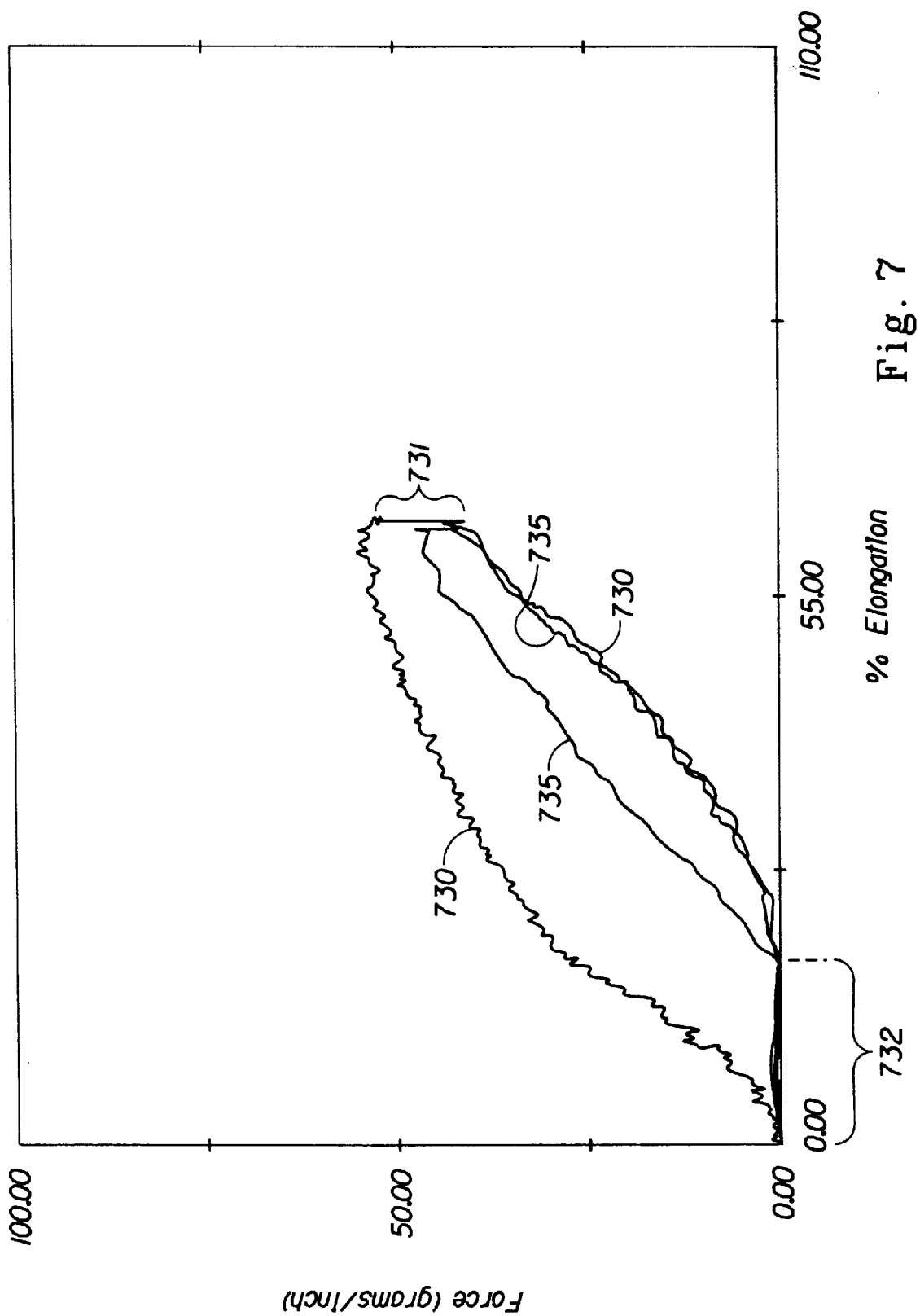
FIG. 7 is a graph of the elastic hysteresis behavior of the SELF web of FIG. 6 when subjected to 60% elongation and examined for hysteresis response.

The curves 730 and 735 in FIG. 7 show the elastic hysteresis behavior exhibited by the SELF web of the present invention which is generally similar to the SELF web used to generate curve 720 in FIG. 6. The SELF web was examined for elastic hysteresis behavior at an elongation of 60%. Curve 730 represents the response to an applied and released elongation during the first cycle and curve 735 represents the response to applied and released elongation during the second cycle. The force relaxation during the first cycle 731 and the percent set or deformation 732 are depicted in FIG. 7. Note that significant recoverable elongation, or useful elasticity, is exhibited at relatively low forces over multiple cycles, i.e., the SELF web can easily expand and contract to a considerable degree. The method for generating the elastic hysteresis behavior can be found in the Test Method section in the subsequent portion of the specification.

When the SELF web is subjected to an applied elongation, the SELF web exhibits an elastic-like behavior as it extends in the direction of applied elongation and returns to its substantially untensioned condition once the applied elongation is removed, unless the SELF web is extended beyond the point of yielding. The SELF web is able to undergo multiple cycles of applied elongation without losing its ability to substantially recover. Accordingly, the SELF web is able to return to its substantially untensioned condition once the applied elongation or force is removed.

While the SELF web may be easily and reversibly extended in the direction of applied axial elongation, in a direction substantially perpendicular to the first axis of the rib-like elements, the SELF web is not as easily extended in a direction substantially parallel to the first axis of the rib-like elements. The formation of the rib-like elements allows the rib-like elements to geometrically deform in a direction substantially perpendicular to the first or major axis of the rib-like elements, while requiring substantially molecular-level deformation to extend in a direction substantially parallel to the first axis of the rib-like elements.

The amount of applied force required to extend the SELF web is dependent upon the composition and cross-sectional area of the web material forming the SELF web and the width and spacing of the first regions, with narrower and more widely spaced first regions requiring lower applied extension forces to achieve the desired elongation. The first axis, (i.e., the length) of the first regions is preferably greater than the second axis, (i.e., the width) of the first region with a preferred length to width ratio of from about 5:1 or greater.

The depth and frequency of rib-like elements can also be varied to control the available stretch of the SELF web. The available stretch is increased if for a given frequency of rib-like elements, the height or degree of deformation imparted on the rib-like elements is increased. Similarly, the available stretch is increased if for a given height or degree of deformation, the frequency of rib-like elements is increased.

While the entire SELF web includes a strainable network of first and second regions, the present invention may also be practiced by providing specific portions of the SELF web with a strainable network comprised of first and second regions. For example, only the side panels 57 of the waist belt 32 need include the discrete, strainable networks. Thus, all or a portion of the extensible belt may include a strainable network comprised of first and second regions to provide an extensible waist belt exhibiting a controlled extensional response along a predetermined axis when subjected to an applied axial elongation.

The SELF web also need not be extensible only in the direction parallel to the lateral centerline of the diaper as is shown in FIG. 1. For example, the longitudinal axis and the transverse axis of the SELF web may be disposed at an angle to the longitudinal centerline and lateral centerline of the diaper 20, respectively. Thus, the SELF web would axially elongate along a line at an angle to the lateral centerline of the diaper. This angle is preferably between about 0° and about 30° for the diapers of the present invention. Further, portions of the SELF web may have different angles of extensibility. For example, in the side panels, a portion of the side panel closest to the end edge of the diaper, a waist panel, may be extensible in a direction parallel to the lateral centerline of the diaper, however, the portion of the SELF web closest to the lateral centerline, the thigh panel, may have an extensibility nonparallel to the direction of extensibility of the waist panel such that it is disposed at an angle to the lateral centerline. This multi-directional SELF panel can provide improved waist and leg conformity.

Figure 8:
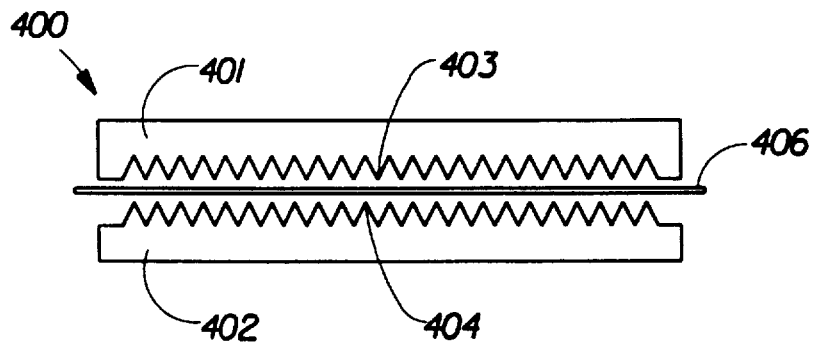
FIG. 8 is a simplified side elevational view of a preferred apparatus used to form that portion of the SELF web of the present invention.

Referring now to FIG. 8, there is shown an apparatus 400 used to form the SELF web 52 shown in FIG. 5. Apparatus 400 includes plates 401, 402. Plates 401, 402 include a plurality of intermeshing teeth 403, 404, respectively. Plates 401, 402 are brought together under pressure to form the base film 406.

Figure 9:
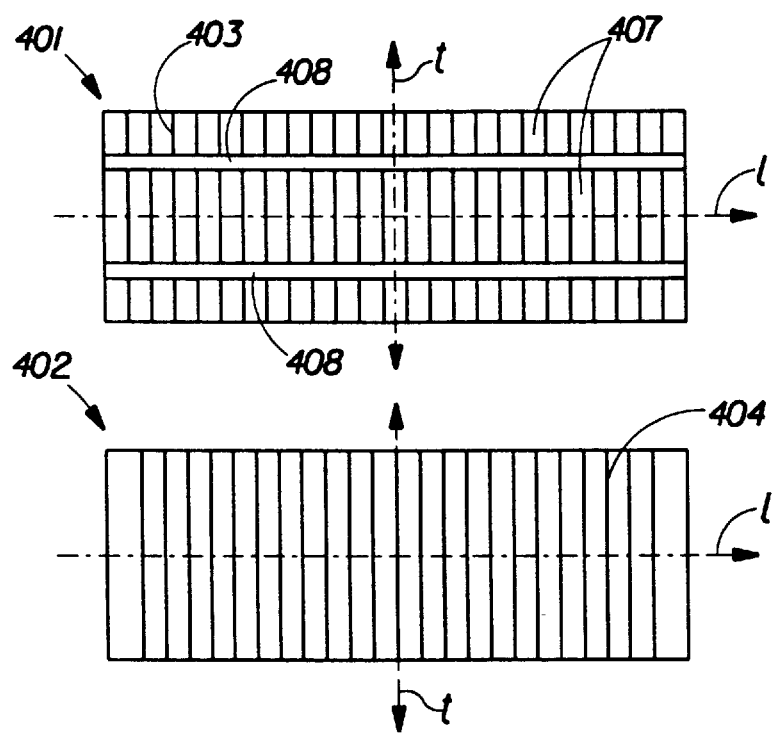
FIG. 9 is a plan view of the opposed meshing plates of the apparatus of FIG. 8 laid side-by-side with their meshing surfaces exposed.

Referring now to FIG. 9, it can be seen that plates 401 and 402 each have a longitudinal axis "l" and a transverse axis "t" which is substantially perpendicular to the longitudinal axis. Plate 401 includes toothed regions 407 and grooved regions 408 both which extend substantially parallel to the longitudinal axis of the plate 401. Within toothed regions 407 of plate 401 there are a plurality of teeth 403. Plate 402 includes teeth 404 which mesh with teeth 403 of plate 401. When the base film 406 is formed between plates 401, 402 the portions of the base film 406 which are positioned within grooved regions 408 of plate 401 and teeth 404 on plate 402 remain undeformed. These regions correspond with the first regions 64 of the SELF web 52 shown in FIG. 5. The portions of the base film 406 positioned between toothed regions 407 of plate 401 and teeth 404 of plate 402 are incrementally and plastically formed creating rib-like elements 74 in the second regions 66 of the SELF web 52.

Figure 10:
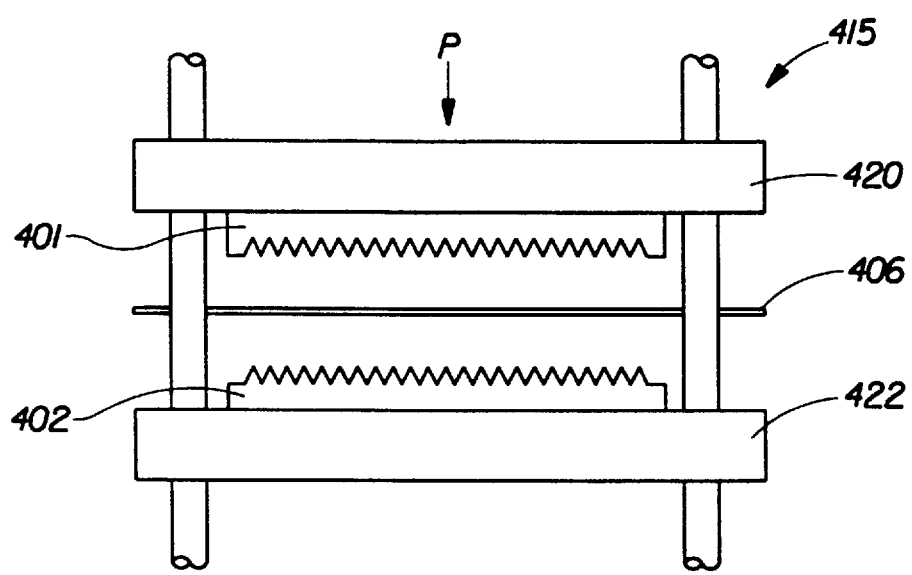
FIG. 10 is a simplified side elevational view of a static press used to form at least a portion of the base film into a SELF web of the present invention.

The method of formation can be accomplished in a static mode, where one discrete portion of a base film is deformed at a time. An example of such a method is shown in FIG. 10. A static press indicated generally as 415 includes an axially moveable plate or member 420 and a stationary plate 422. Plates 401 and 402 are attached to members 420 and 422, respectively. While plates 401 and 402 are separated, base film 406 is introduced between the plates, 401, 402. The plates are then brought together under a pressure indicated generally as "P". The upper plate 401 is then lifted axially away from plate 402 allowing the formed polymeric web to be removed from between plates 401 and 402.

Figure 11:
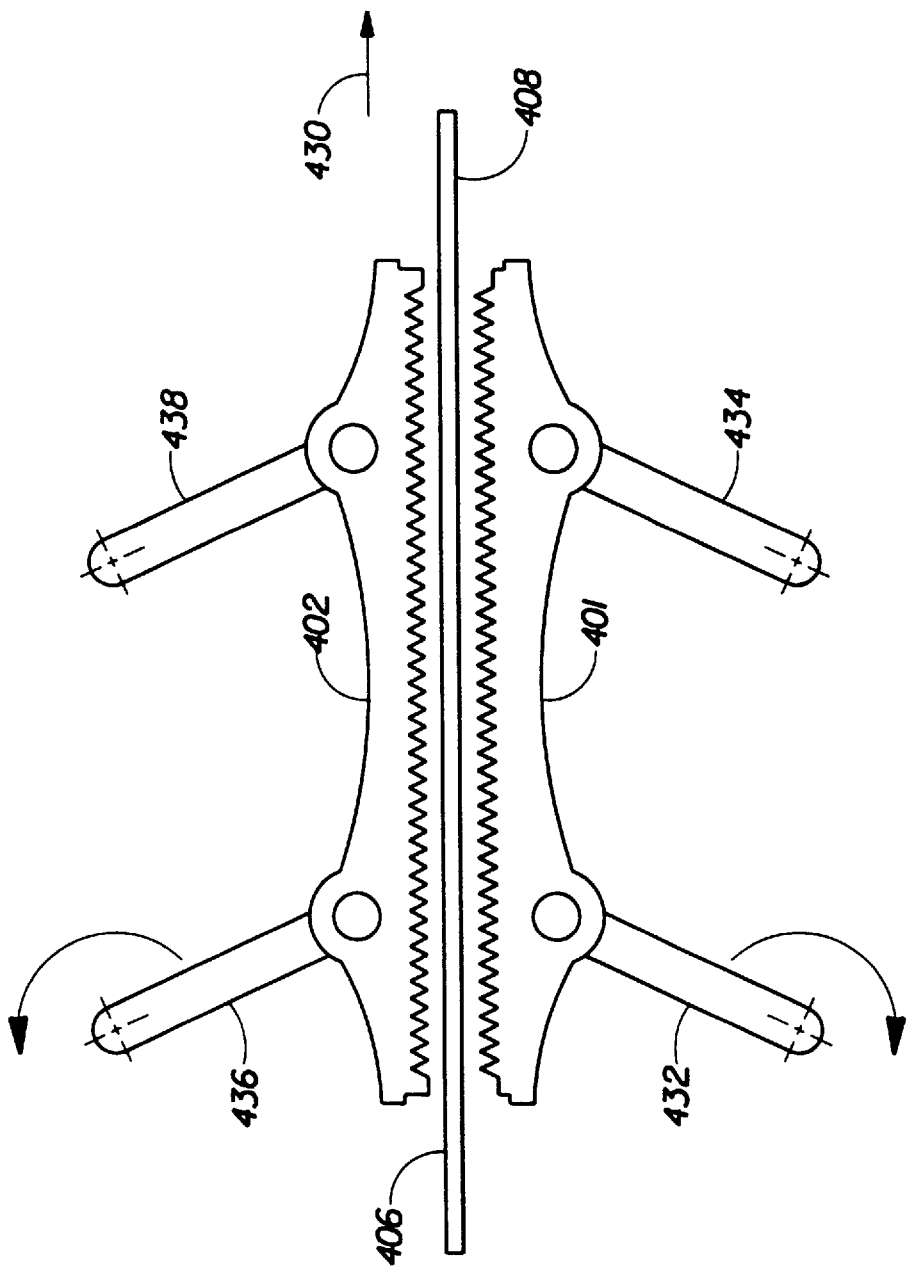
FIG. 11 is a simplified side elevational view of a continuous, dynamic press used to form predetermined portions of the base film into a SELF web of the present invention.

FIG. 11 is an example of a dynamic press for intermittently contacting the moving web and forming the base material 406 into a formed web similar to the SELF web 52 of FIG. 5. Polymeric film 406 is fed between plates 401 and 402 in a direction generally indicated by arrow 430. Plate 401 is secured to a pair of rotatably mounted arms 432, 434 which travel in a clockwise direction which move plate 401 in a similar clockwise motion. Plate 402 is connected to a pair of rotary arms 436, 438 which travel in a counter clockwise direction moving plate 402 in a counter clockwise direction. Thus, as web 406 moves between plates 401 and 402 in direction indicated by arrow 430, a portion of the base film between the plates is formed and then released such that the plates 401 and 402 may come back grab and deform another section of base film 406. This method has the benefit of allowing virtually any pattern of any complexity to be formed in a continuous process, e.g., uni-directional, bi-directional, and multi-directional patterns.

The dynamic press of FIG. 11 could be used on a completed absorbent article to form strainable networks into the completed product. For example, the entire or portions of the completed absorbent article could be placed between plates 401 and 402 to create a strainable network in all layers of the absorbent article.

Another method of forming the base material into a SELF web is vacuum forming. An example of a vacuum forming method is disclosed in commonly assigned U.S. Pat. No. 4,342,314, issued to Radel et al. on Aug. 3, 1982. Alternatively, the SELF web of the present invention may be hydraulically formed in accordance with the teachings of commonly assigned U.S. Pat. No. 4,609,518 issued to Curro et al. on Sep. 2, 1986. Each of the above said patents being incorporated herein by reference.

Figure 12:
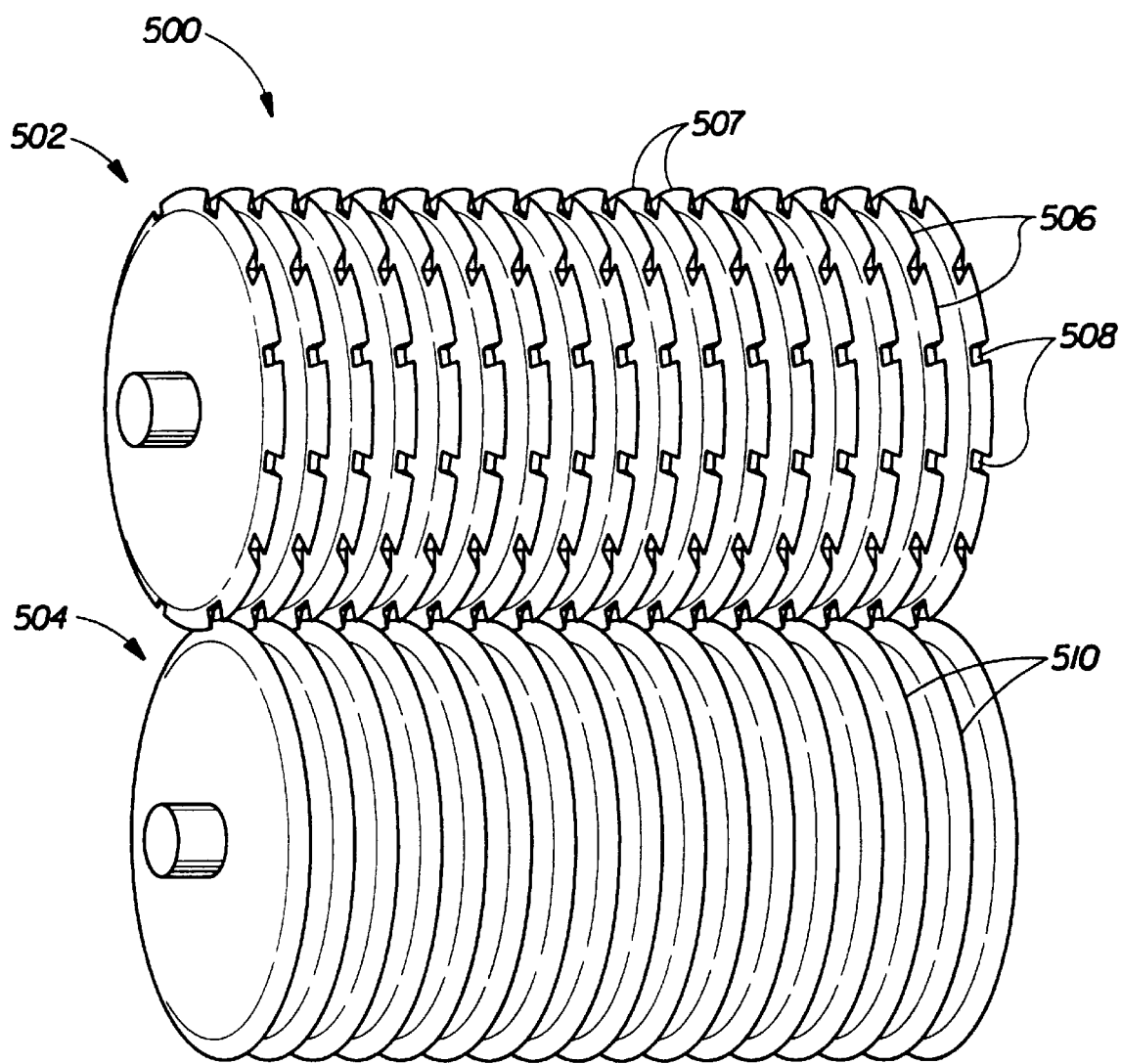
FIG. 12 is a simplified illustration of an apparatus used to form at least a portion of a base film into a SELF web of the present invention.

In FIG. 12 there is shown another apparatus generally indicated as 500 for forming the base film into a formed SELF web. Apparatus 500 includes a pair of rolls 502, 504. Roll 502 includes a plurality of toothed regions 506 and a plurality of grooved regions 508 that extend substantially parallel to a longitudinal axis running through the center of the cylindrical roll 502. Toothed regions 506 include a plurality of teeth 507. Roll 504 includes a plurality of teeth 510 which mesh with teeth 507 on roll 502. As a base film is passed between intermeshing rolls 502 and 504, the grooved regions 508 will leave portions of the film undeformed producing the first regions of the SELF web 52 of FIG. 5. The portions of the film passing between toothed regions 506 and teeth 510 will be formed by teeth 507 and 510, respectively, producing rib-like elements in the second regions of the SELF web 52.

Alternatively, roll 504 may consist of a soft rubber. As the base film is passed between toothed roll 502 and rubber roll 504 the film is mechanically formed into the pattern provided by the toothed roll 502. The film within the grooved regions 508 will remain undeformed, while the film within the toothed regions 506 will be formed producing rib-like elements in the second regions.

Figure 13:
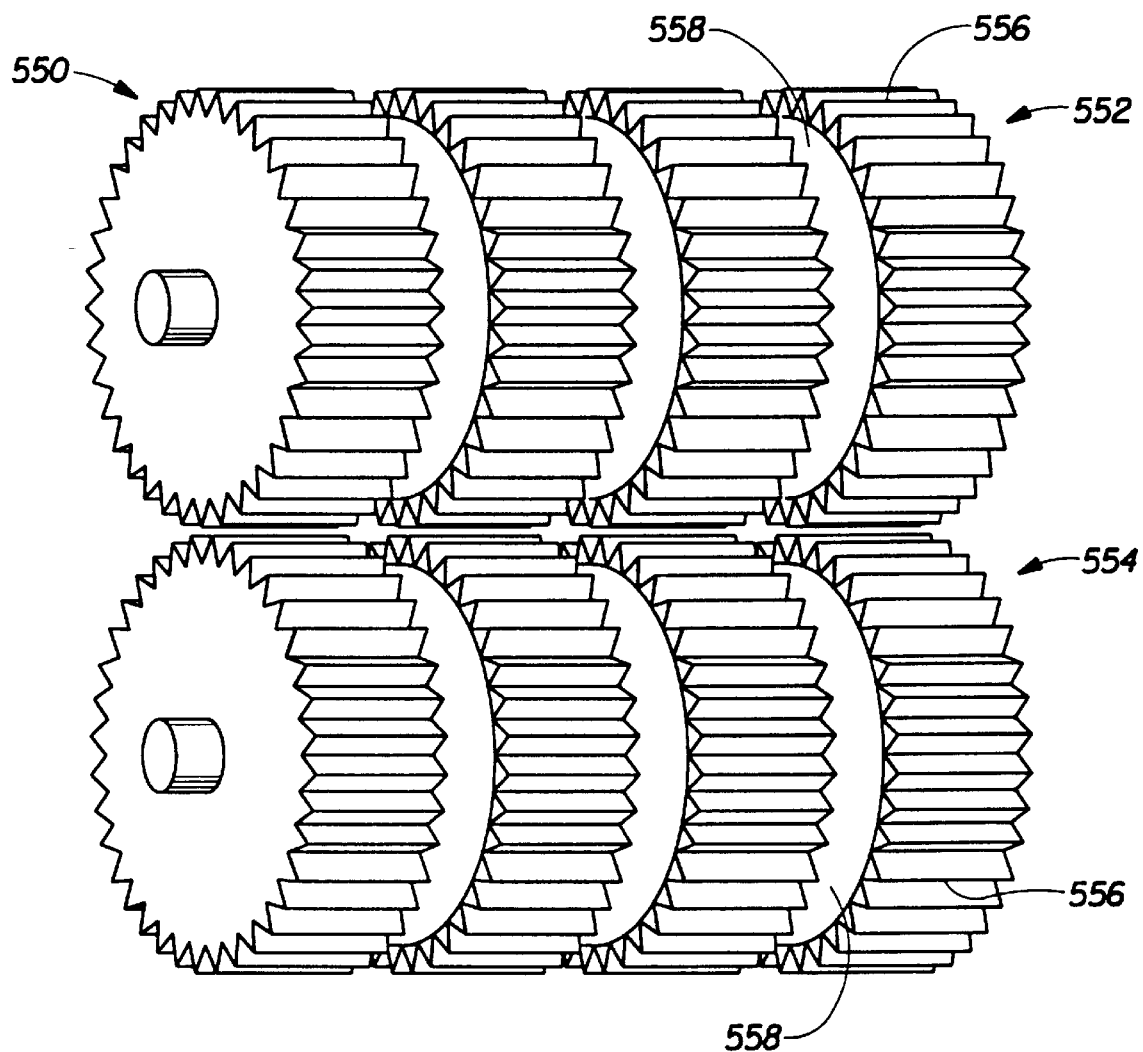
FIG. 13 is a simplified illustration of yet another apparatus used to form at least a portion of a base film into a SELF web of the present invention.

Referring now to FIG. 13, there is shown an alternative apparatus generally indicated as 550 for forming the base film into a SELF web in accordance with the teachings of the present invention. Apparatus 550 includes a pair of rolls 552, 554. Rolls 552 and 554 each have a plurality of toothed regions 556 and grooved regions 558 extending about the circumference of rolls 552, 554 respectively. As the base film passes between rolls 552 and 554, the grooved regions 558 will leave portions of the film unformed, while the portions of the film passing between toothed regions 556 will be formed producing rib-like elements in second regions 66.

Web material of the present invention may be comprised of polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE® available from Dow Chemical Company and EXXACT® available from Exxon), and breathable polymers. The web materials may also be comprised of a synthetic woven, synthetic knit, nonwoven, apertured film, macroscopically expanded three-dimensional formed film, absorbent or fibrous absorbent material, foam filled composition or laminates and/or combinations thereof. The nonwovens may be made but not limited to any of the following methods: spunlace, spunbond, meltblown, carded and/or air-through or calender bonded, with a spunlace material with loosely bonded fibers being the preferred embodiment.

While the SELF web has been described as a single base layer of substantially planar polymeric film, the present invention may be practiced equally well with other base materials or with laminates of materials. Examples of base materials from which the SELF web of the present invention can be made include two-dimensional apertured films and macroscopically expanded, three-dimensional, apertured formed films. Examples of macroscopically expanded, three-dimensional, apertured formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference. Examples of other suitable base materials include composite structures or laminates of polymer films, nonwovens, and polymer films and nonwovens. The laminates of polymer films and nonwovens may also comprise absorbent or fibrous absorbent materials, foams, or other compositions. Additional reinforcing elements can also be added for strength and recovery benefits.

Base materials comprising laminates of apertured films and nonwoven materials may also be used whereby in the process of forming such materials, the connections between a plurality of the nonwoven fibers are broken up to protrude slightly through the apertures of the apertured film.

It may be desirable in certain embodiments to have the SELF web exhibit a certain degree of bulkiness. Laminates of polymer films with high-loft nonwoven materials, and laminates with multi-layers of nonwovens are ways of providing increased bulk. Other methods for creating bulk include the formation of a single layer of polymer film in the manner of this invention followed by prestretching of the film and subsequent application of the nonwoven to one or both sides while the polymer film is in its prestretched condition. Upon relaxation of the stretch, the nonwoven material forms puckers which give the material added bulk. Another method for making bulky laminates is by forming individual polymeric film layers in the manner of this invention, followed by lamination of multiple layers of these materials. Three dimensionally apertured films that have been formed using the method described herein also provide good bulk in a laminate structure.

Other materials which may be subject to the deformation processes disclosed herein for producing webs which exhibit an elastic-like behavior in the direction of applied force include polymeric foams and thermally bonded air-laid fibrous structures.

Figure 14:
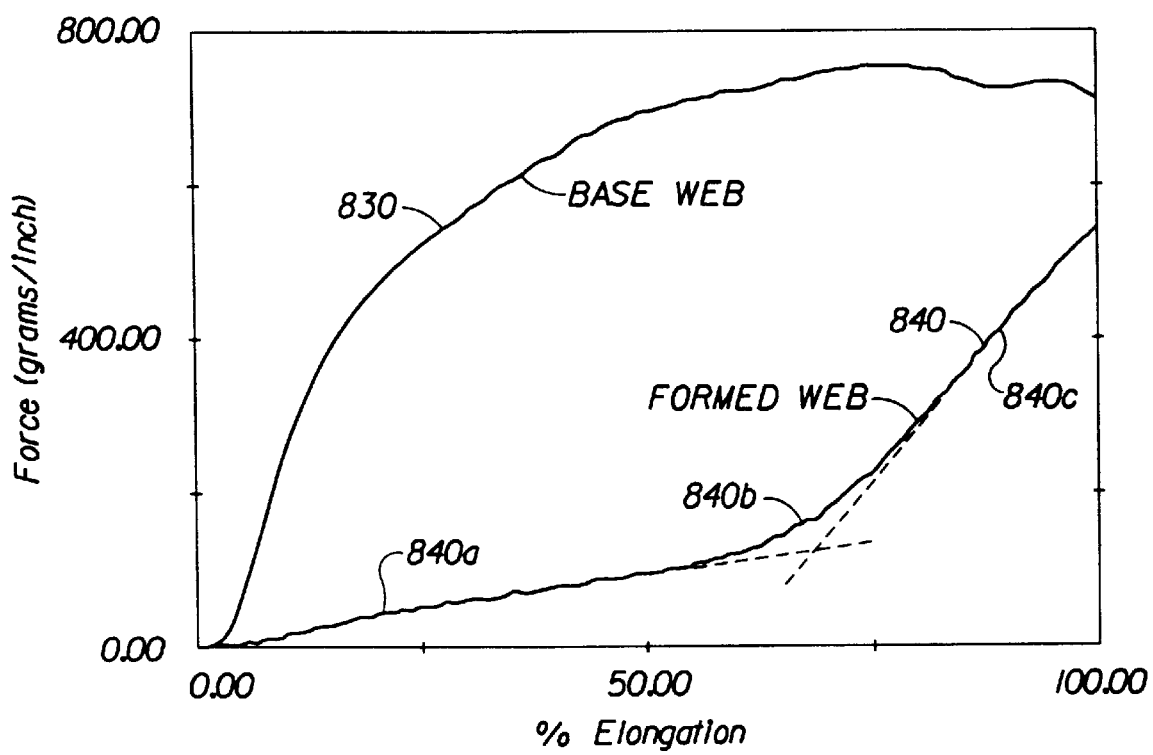
FIG. 14 is a graph of the resistive force vs. percent elongation comparing the behavior of an alternative SELF web material which is a laminate comprised of a layer of a polymeric film, and a nonwoven layer secured by adhesive having a strainable network of the present invention to the otherwise identical unformed, planar, base web material.
Figure 15:
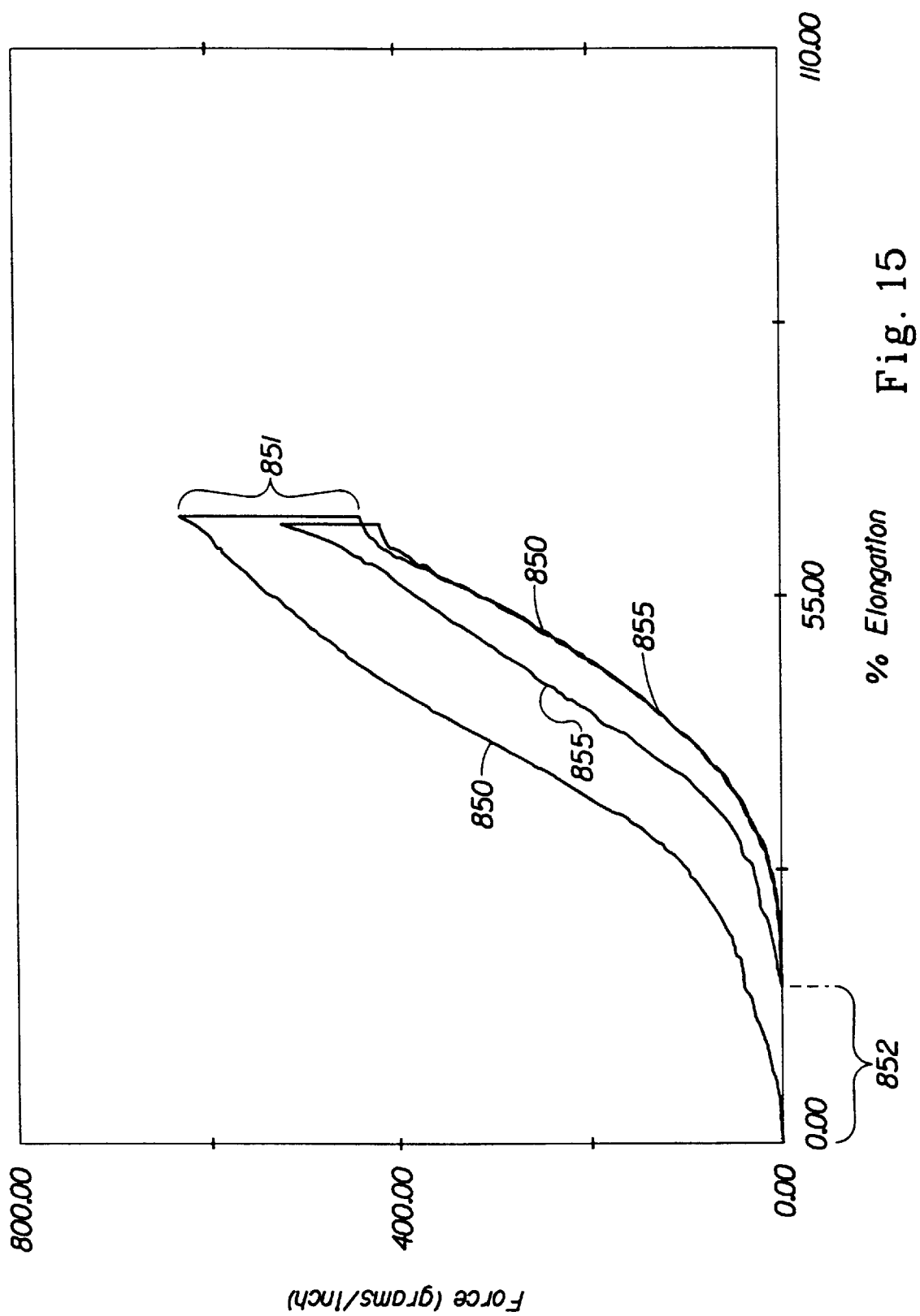
FIG. 15 is a graph of the elastic hysteresis behavior of the web material having the strainable network of FIG. 14 when subjected to 60% percent elongation and examined for elastic hysteresis response.

FIG. 14 shows the force elongation behavior for both a base web depicted by curve 830 and a formed SELF web depicted by the curve 840 where both webs are comprised of a laminate of a layer of the Clopay 1401 polyethylene blend film adhered via hot melt glue available from Findley Adhesives, of Wauwautosa, Wis., Sample 2301, to a layer of nonwoven material made substantially of polypropylene fibers as is available from Veratec of Walpole, Mass., under the designation P-11. Referring now to curve 840, there is an initial substantially linear, lower force-elongation stage I designated 840a, a transition zone designated 840b, and substantially linear stage II designated 840c. For this laminate web, note the distinctive lower force two-stage behavior of the formed SELF web provided in first stage I (840*a*) by the combination of molecular-level deformation of the first region and geometric deformation of the second region and then in stage II (840*c*) by molecular-level deformation of both the first region and a second region as depicted in curve 840 compared to the molecular-level deformation of the base web as depicted in curve 830. The curves 850 and 855 in FIG. 15 show the elastic hysteresis behavior of a formed web material similar to the formed web material used to generate curve 840 in FIG. 14 examined at 60% elongation. Curve 850 represents the response to an applied and released elongation during the first cycle and curve 855 represents the response to applied and released elongation during the second cycle. The force relaxation during the first cycle 851 and the percent set of the web after the first cycle 852 are shown in FIG. 15. Note that this laminate web exhibits a very significant elastic recovery over the observed range of elongation over multiple cycles.

In a preferred embodiment of the present invention, as is shown in FIG. 2, the SELF web comprises a laminate of three layers comprising an inner layer 53, an outer layer 55, and a support layer 54. The inner layer 53 is preferably a nonwoven material such as the P-8 material previously described. The outer layer 55 is preferably the base polymeric film as described herein with reference to FIG. 5. The support layer 54 is preferably a formed film such as the DRI-WEAVE material as marketed by The Procter & Gamble Company of Cincinnati, Ohio. Alternatively, the support layer may be eliminated to provide a lower cost two layer laminate of a nonwoven and the base polymeric film. Further, a nonwoven layer may be added over the outer layer to provide a softer feel for the outside of the waist belt. The laminates may be combined by any of a number of bonding methods known to those skilled in the art. Such bonding methods include but are not limited to thermal bonding; adhesive bonding (using any of a number of adhesives including but not limited to spray adhesives, hot melt adhesives, latex based adhesives and the like); sonic bonding; and extrusion laminating whereby a polymeric film is cast directly onto a nonwoven substrate, and while still in a partially molten state, bonds to one side of the nonwoven or where a meltblown nonwoven is directly attached to a polymeric web.

The waist belt 32 is joined to the chassis assembly 22 by a belt attachment element 50. The belt attachment element 50 may comprise any of the known attachment means as are discussed herein including adhesive, heat bonds, pressure bonds, ultrasonic bonds dynamic mechanical bonds or combinations of these. Preferably, the belt attachment element is an adhesive, preferably an open pattern network of adhesive filaments as described herein. The waist belt 32 is preferably directly joined to the chassis assembly 22 with the inner layer 53 being directly joined to the backsheet 26. Alternatively, the waist belt 32 may be joined between the topsheet 24 and the backsheet 26, between other elements of the diaper 20, or directly to other elements of the diaper including, for example, directly joining the outer layer 55 to the topsheet 24.

The diaper 20 is also preferably provided with a closure system for fitting the diaper on the wearer. While the closure system may take on a number of configurations such as adhesive tape tabs, mechanical closure tape tabs, fixed position fasteners, or any other closure means as are known in the art; as shown in FIG. 1, the closure system preferably comprises an adhesive tape tab fastening system including a pair of tape tabs 34 and a landing zone (not shown) positioned in the first waist region 40 of the chassis assembly 22. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference.

The diaper 20 is preferably applied to a wearer by positioning one of the waist regions, preferably the second waist region 42, under the wearer's back and drawing the remainder of the diaper between the wearer's legs so that the other waist region, preferably the first waist region 40, is positioned across the front of the wearer. The tab portions of the tape tabs 34 are then released from the release portion. The diaperer then wraps the extensible waist belt 32 around the wearer, while still grasping the tab portion. The extensible waist belt 32 will typically be extended and tensioned during this operation so as to conform to the size and shape of the wearer. The tape tab 34 is secured to the landing zone on the chassis assembly 22 to effect a side closure. The process is then repeated with the other tape tab. Thus, the diaper is closed on the wearer and the waist belt 32 comprised of the SELF web provides the fit and containment benefits as described herein.

Alternatively, the waist belt may be provided with a closure system that allows the side panels to be first joined together. The diaperer then brings the chassis assembly between the legs of the wearer and joins the chassis assembly to the outer layer of the waist belt. Such a configuration and securing method is more fully described in the above-referenced U.S. application Ser. No. 08/044,562 to New, et al.

For comparison purposes, a number of different commercially available large disposable diaper products designated Samples A–F and a large diaper product of the present invention designated Sample X were measured. The data from these measurements is set forth in the following tables:

TABLE I

| Diaper | Area of Chassis (cm$^2$) | Area of Absorbent Core (cm$^2$) | Ratio of Absorbent Core Area to Chassis Area |
|---|---|---|---|
| Sample X | 909 | 342 | 0.376:1.0 |
| Sample A | 1289 | 570 | 0.442:1.0 |
| Sample B | 1316 | 576 | 0.438:1.0 |
| Sample C | 1313 | 707 | 0.538:1.0 |
| Sample D | 1260 | 565 | 0.448:1.0 |
| Sample E | 1266 | 559 | 0.442:1.0 |
| Sample F | 1234 | 635 | 0.514:1.0 |

Referring to Table I, the commercially available products tested were all designated for use on large infants on their respective packages. Sample X product is intended to be used on large infants. The chassis area of the diapers was determined by first freezing and then removing the elastic elements from each of the diapers. The absorbent core was then removed from each of the diapers. Each diaper was then placed in its flat out condition on a piece of paper having a known area and basis weight. The perimeter of the diaper chassis was then traced onto the paper. The paper was then cut along the traced line. The cut out piece of paper was then weighed. The area of the chassis was then calculated based on the known area and basis weight of the piece of paper prior to being cut. A similar procedure was then used to calculate the area of the absorbent core.

As can be seen from the data in Table I, the Sample X diaper of the present invention has the smallest ratio of absorbent core area to chassis area of the samples tested. Other embodiments of disposable diapers of the present invention preferably have a ratio of absorbent core area to chassis area of less than about 0.40:1.0, more preferably less than about 0.39:1.0; and most preferably less than about 0.38:1.0. One disposable diaper embodiment has a ratio of absorbent core area to chassis area of about 0.38:1.0.

Referring again to Table I, it will be noted that the Sample X diaper of the present invention has an absorbent core area and chassis area substantially less than the other commercially available diapers tested. Because of the unique design of the diaper of the present invention, the absorbent core of the diaper of the present invention is able to cover a substantial amount of the wearer's crotch area while using significantly less chassis material and absorbent core material.

Figure 16:
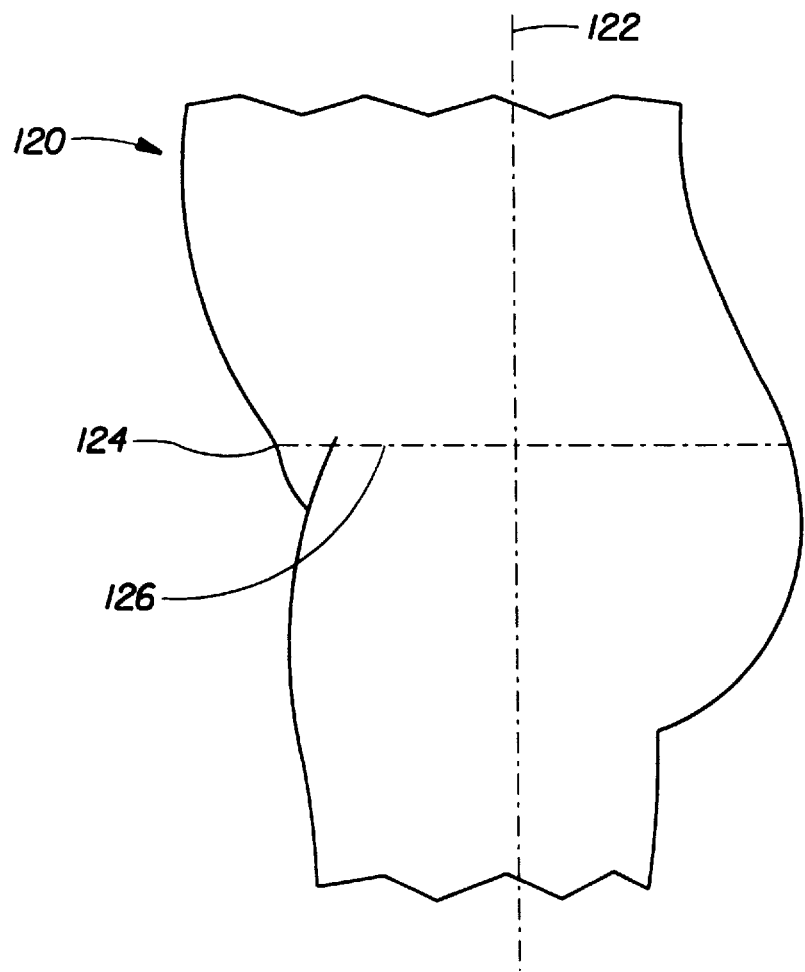
FIG. 16 is a side view illustration of the torso of the body of a wearer.

Referring now to FIG. 16, a side view illustration of a wearer's torso of a wearer is shown, generally indicated as 120. The torso 120 is shown with the body in an upright or standing position. The wearer or torso has an upright axis 122. The upright axis 122 of the wearer extends through the torso in a direction substantially perpendicular to a surface upon which the wearer is standing, e.g., the floor or ground. The pubic bone is indicated as 124. Plane 126, which defines the uppermost end of the crotch, extends from the pubic bone 124 through the torso in a direction perpendicular to the upright axis 122.

For comparison purposes the area of the crotch covered by the absorbent core of a Sample X diaper of the present invention and the Sample D diaper were measured. The Sample D diaper was chosen for comparison from the commercially available diapers in Table I, as it represents a typical commercially available diaper as can be seen from the data in Table I. The data from the measurements is set forth in the following table:

TABLE II

| Weight of Baby (lbs) | Crotch Area Covered by Absorbent Core of Sample X Diaper (cm²) | Crotch Area Covered by Absorbent Core of the Sample D Diaper (cm²) |
| --- | --- | --- |
| 21.5 | 137.12 | 157.15 |
| 23.5 | 140.47 | 160.13 |
| 25.5 | 147.26 | 168.96 |
| 27.5 | 153.77 | 176.22 |
| 29.5 | 164.75 | 179.70 |
| 31.5 | 162.82 | 183.17 |
| 33.5 | 167.77 | 191.38 |
| 35.5 | 181.85 | 210.20 |

Referring to Table II, the crotch area covered was determined using an empirical computer model. The inputs into the model are the geometry and material properties of the diaper, and a population of babies which includes their weight and shape. The model then places the diaper onto the population of babies and measures various parameters such as the crotch area covered by the absorbent core. While a computer model was used to generate the data in Table II, the data may also be generated by manually measuring the crotch area covered by the absorbent core. As can be seen from the data in table Table II, the amount of crotch area covered by the Sample X diaper is less than the crotch area covered by the Sample D diaper.

The Sample X diaper of the present invention covers less crotch area than the commercially available diaper, but as can be seen from the data in Table I, the Sample X diaper has an absorbent core area which is substantially less than the absorbent core areas of the diapers tested. The efficiencies of the of Sample X diaper and the commercially available diapers, represented by the Sample D diaper, is set forth in the following table:

TABLE III

| Weight of Baby (lbs) | Ratio of Crotch Area Covered by Absorbent Core to Area of Absorbent Core of Sample X Diaper | Ratio of Crotch Area Covered by Absorbent Core to Area of Absorbent Core of the Sample D Diaper |
| --- | --- | --- |
| 21.5 | 0.40:1.0 | 0.28:1.0 |
| 23.5 | 0.41:1.0 | 0.28:1.0 |
| 25.5 | 0.43:1.0 | 0.30:1.0 |
| 27.5 | 0.45:1.0 | 0.31:1.0 |
| 29.5 | 0.48:1.0 | 0.31:1.0 |
| 31.5 | 0.48:1. | 0.32:1.0 |
| 33.5 | 0.49:1.0 | 0.34:1.0 |
| 35.5 | 0.53:1.0 | 0.37:1.0 |

Referring now to Table III, it will be noted that the ratios of the wearer's crotch area covered by the absorbent core to the area of the absorbent core of the Sample X diaper are greater than the ratios of the commercially available diaper. Diapers of the present invention preferably have a ratio of the wearer's crotch area covered by the absorbent core of at least 0.40:1.0.

TABLE IV

| Diaper | Maximum Width of Chassis in First Waist Region (cm) | Maximum Width of Chassis in Second Waist Region (cm) | Ratio of Widths in Waist Regions |
| --- | --- | --- | --- |
| Sample X | 180 | 324 | 1.8:1 |
| Sample A | 334 | 334 | 1:1 |
| Sample B | 341 | 341 | 1:1 |
| Sample C | 340 | 340 | 1:1 |
| Sample D | 335 | 335 | 1:1 |
| Sample E | 335 | 335 | 1:1 |
| Sample F | 333 | 333 | 1:1 |

Referring now to Table IV, it will be noted that the Sample X diaper has the largest ratio of width of chassis in first waist region to width of chassis in second waist region of the samples tested. Other embodiments of the disposable diapers of the present invention preferably have a ratio of width of chassis in first waist region to width of chassis in second waist region of at least 1.3:1, more preferably of at least 1.5:1, and most preferably of at least 1.7:1.

TABLE V

| Diaper | Length of Chassis (cm) | Area of Chassis (cm2) | Ratio of Length of Chassis to Area of Chassis (cm/cm²) |
| --- | --- | --- | --- |
| Sample X | 46.0 | 909 | 0.506:1.0 |
| Sample A | 47.5 | 1289 | 0.369:1.0 |
| Sample B | 49.0 | 1316 | 0.372:1.0 |
| Sample C | 49.3 | 1313 | 0.376:1.0 |
| Sample D | 50.0 | 1260 | 0.397:1.0 |
| Sample E | 49.8 | 1266 | 0.393:1.0 |
| Sample F | 49.5 | 1234 | 0.401:1.0 |

Referring now to Table V, it will be noted that the Sample X diaper has the largest ratio of length of chassis to area of chassis of the samples tested. Other embodiment of disposable diapers of the present invention preferably have a ratio of length of chassis to area of chassis of at least 0.45:1.0 (cm/cm$^2$), more preferably of at least 0.48:1.0 (cm/cm$^2$), and most preferably of at lesat 0.50:1.0 (cm/cm$^2$). One disposable diaper embodiment of the present invention has a ratio of length of chassis to area of chassis of about 0.51:1.0 (cm/cm$^2$).

Figure 3:
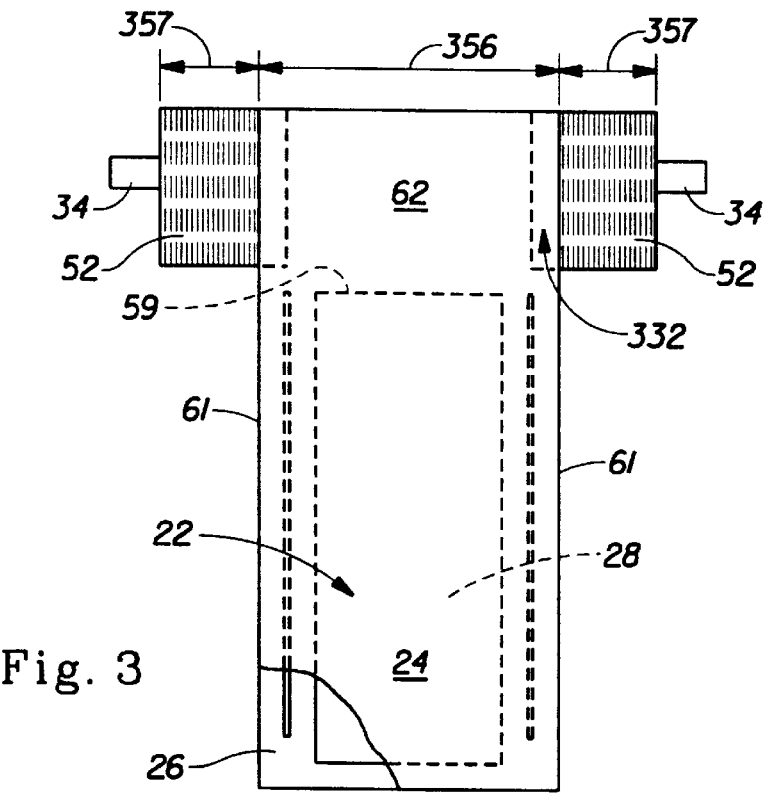
FIG. 3 is a plan view of an alternative diaper embodiment of the present invention.

FIG. 3 shows an alternative embodiment of the present invention wherein the waist belt 332 is formed from separate materials joined together. In this embodiment, the side panels 357 are each a separate material, preferably the SELF web 52 as described herein, joined adjacent to the leg edge 61 of the chassis assembly 22. The central waist panel 356 is formed by a portion of the chassis assembly 22, in this embodiment the end flap 62 formed by the extension of the topsheet 24 and the backsheet 26 beyond the waist edge 59 of the absorbent core 28. Thus, in this embodiment, the central waist panel 356 is not extensible but the side panels 357 are since they are constructed of the SELF web 52.

Figure 4:
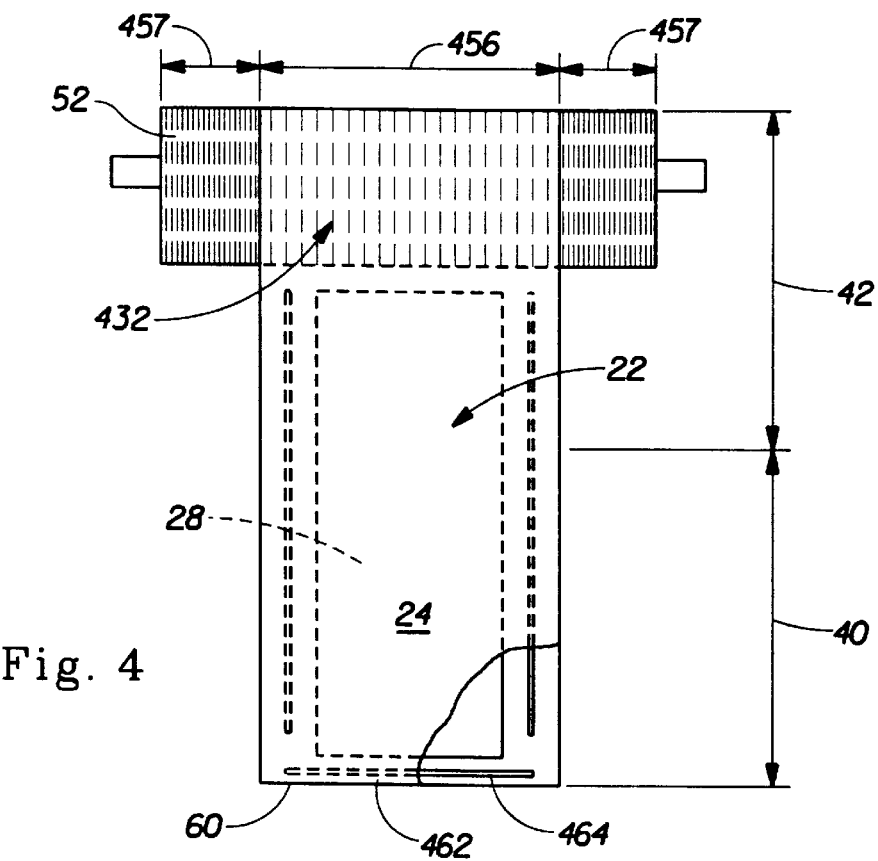
FIG. 4 is a plan view of a further alternative diaper embodiment of the present invention.

FIG. 4 shows a further alternative embodiment of the present invention wherein the waist belt 432 is formed from a continuous SELF web and a portion of the chassis assembly 22. In this embodiment, the SELF web 52 extends across the entire diaper in the second waist region 42. The chassis assembly 22 is joined to the SELF web 52 in the central waist panel 456. While the central waist panel 456 may be nonextensible since the components of the chassis assembly 22 are nonextensible, in the preferred embodiment as shown in FIG. 4, the central waist panel 456 is subjected to mechanical straining to allow the central waist panel 456 to have some degree of extensibility or to the SELF processes as described herein such that the waist belt 432 is entirely a SELF web. This extensibility is shown by the dashed lines in FIG. 4. The lateral edge 60 of the chassis assembly 22 in the first waist region 40 is also provided with an elasticized waistband 462 by operatively associating an elastic member 464 with the chassis assembly 22, preferably with either the topsheet 24, the backsheet 26, or both, more preferably between the topsheet 24 and the backsheet 26. Examples of such elasticized waistbands are disclosed in U.S. Pat. No. 5,151,092 issued to Buell, Clear and Falcone on Sep. 29, 1992; or in U.S. Pat. No. 4,515,595 issued to Kievit and Osterhage on May 7, 1985; each of which are incorporated herein by reference. Alternatively, the lateral edge of the chassis assembly in the first waist region may also comprise a SELF web as described herein.

In an alternative embodiment of the present invention, the diaper may also be provided with ear flaps that extend laterally outwardly from each leg edge of the chassis assembly in the first waist region. The ear flaps provide a structure to which the waist belt can be attached to encircle the legs and waist of the wearer. The ear flaps may take on a number of different sizes, shapes, configurations, and materials. The ear flaps may comprise a portion of the material making up one or more of the diaper elements, including the topsheet, and the backsheet. Alternatively, the ear flaps may comprise a separate element or a plurality of elements affixed to the diaper. Suitable materials for use as the ear flaps include woven webs; nonwoven webs; films, including polymeric films; foams; laminate materials including film laminates, nonwoven laminates, or zero strain laminates; elastomers; composites; SELF webs; or any combination of these materials. The ear flaps may be joined to the chassis assembly by any means as are known in the art; for example, the ear flaps may be continuously or intermittently bonded to the chassis assembly using heated or unheated adhesive, heat bonding, pressure bonding, ultrasonic bonding, dynamic mechanical bonding or any other method that is known in the art.

Test Methods

Surface-Pathlength

Pathlength measurements of formed material regions are to be determined by selecting and preparing representative samples of each distinct region and analyzing these samples by means of microscopic image analysis methods.

Samples are to be selected so as to be representative of each region's surface geometry. Generally, the transition regions should be avoided since they would normally contain features of both the first and second regions. The sample to be measured is cut and separated from the region of interest. The "measured edge" is to be cut parallel to a specified axis of elongation. Usually this axis is parallel to the formed primary-axis of either the first region or the second region. An unstrained sample length of one-half inch is to be "gage marked" perpendicular to the "measure edge": while attached to the web material, and then accurately cut and removed from the material region.

Measurement samples are then mounted onto the long-edge of a microscopic glass slide. The "measured edge" is to extend slightly (approximately 1 mm) outward from the slide edge. A thin layer of pressure-sensitive adhesive is applied to the glass face-edge to provide a suitable sample support means. For highly formed sample regions it has been found desirable to gently extend the sample in its axial direction (without imposing significant force) simultaneously to contact and attachment of the sample to the slide-edge. This allows improved edge identification during image analysis and avoids possible "crumpled" edge portions that require additional interpretation analysis.

Images of each sample are to be obtained as "measured edge" views taken with the support slide "edge on" using suitable microscopic measuring means of sufficient quality and magnification. Data herein presented was obtained using the following equipment; Keyence VH-6100 (20× Lens) video unit, with video-image prints made with a Sony Video printer Mavigraph unit. Video prints were image-scanned with a Hewlett Packard ScanJet IIP scanner. Image analysis was on a MacIntosh IICi computer utilizing the software NIH MAC Image version 1.45.

Using this equipment, a calibration image initially taken of a grid scale length of 0.500" with 0.005" increment-marks to be used for calibration setting of the computer image analysis program. All samples to be measured are then video-imaged and video-image printed. Next, all video-prints are image-scanned at 100 dpi (256-level gray scale) into a suitable Mac image-file format. Finally, each image-file (including calibration file) is analyzed utilizing Mac Image 1.45 computer program. All samples are measured with freehand line-measurement tool selected. Samples are measured on both side-edges and the lengths recorded. Simple film-like (thin & constant thickness) samples require only one end-edge to be measured. Laminate and thick foam samples are measured on both side-edges. Length measurement tracings are to be made along the full gage length of a cut sample. In cases of highly deformed samples, multiple (partially overlapping) images may be required to cover the entire cut sample. In these cases, select characteristic features common to both overlapping-images are utilized as "markers" to permit image length readings to adjoin but not overlap.

The final determination of pathlength for each region is obtained by averaging the lengths of five (5) separate ½" gage-samples of each region. Each gage-sample "pathlength" is to be the average of both side-edge surface pathlengths.

Poisson's Lateral Contraction Effect

The Poisson's lateral contraction effect is measured on an Instron Model 1122, as available from Instron Corporation of Canton, Mass., which is interfaced to a Gateway 2000 486/33 Hz computer available from Gateway 2000 of N. Sioux City, S. Dak., using Test Works™ software which is available from Sintech, Inc. of Research Triangle Park, N.C. All essential parameters needed for testing are input in the TestWorks™ software for each test. Data collection is accomplished through a combination of manual sample width measurements, and elongation measurements made within TestWorks™.

The samples used for this test are 1" wide×4" long with the long axis of the sample cut parallel to the direction of the first region of the sample. The sample should be cut with a sharp knife or suitably sharp cutting device designed to cut a precise 1" wide sample. It is important that a "representative sample" should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. In general, an "aspect ratio" of (2:1) for the actual extended tensile portion (11:w1) is to be maintained if possible. Five samples are tested.

The grips of the Instron consist of air actuated grips designed to concentrate the entire gripping force along a single line perpendicular to the direction of testing elongation having one flat surface and an opposing face from which protrudes a half round. No slippage should be permitted between the sample and the grips. The distance between the lines of gripping force should be 2" as measured by a steel rule held beside the grips. This distance will be referred to from here on as the "gage length".

The sample is mounted in the grips with its long axis perpendicular to the direction of applied elongation. An area representative of the overall pattern geometry should be symmetrically centered between the grips. The crosshead speed is set to 10 in/min. The crosshead is moved to the specified strain (measurements are made at both 20 and 60% elongation). The width of the sample at its narrowest point (w2) is measured to be the nearest 0.02" using a steel rule. The elongation in the direction of applied extension is recorded to the nearest 0.02" on the TestWorks software. The Poisson's Lateral Contraction Effect (PLCE) is calculated using the following formula:

$$PLCE = \frac{\frac{|w2 - w1|}{w1}}{\frac{|l2 - l1|}{l1}}$$

where $w_2$=The width of the sample under an applied longitudinal elongation
$w_1$=The original width of the sample
$l_2$=The length of the sample under an applied longitudinal elongation
$l_1$=The original length of the sample (gage length)

Measurements are made at both 20 and 60% elongation using five different samples for each given elongation. The PLCE at a given percent elongation is the average of five measurements.

Hysteresis Test

The hysteresis test is used for measuring the percent set and percent force relaxation of a material. The tests are performed on an Instron Model 1122, available from Instron Corporation of Canton, Mass. which is interfaced to a Gateway 2000 486/33 Hz computer available from Gateway 2000 of N. Sioux City, S. Dak. 57049, using TestWorks™ software which is available from Sintech, Inc. of Research Triangle Park, N.C. 27709. All essential parameters needed for testing are input in the TestWorks™ software for each test (i.e., Crosshead Speed, Maximum percent elongation Point and Hold Times). Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of extensibility of the material, samples should be taken parallel to each direction of stretch.) The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three separate tests at 20, 60 and 100% strain are typically measured for each material. Three samples of a given material are tested at each percent elongation.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gage length". The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of two cycles is generated. A representative graph is shown in FIG. 7. The percent force relaxation is determined by the following calculation of the force data from the first cycle:

$$\frac{\text{Force at Max. \% elongation} - \text{Force after 30 sec. hold}}{\text{Force at Maximum \% elongation (cycle 1)}} \times 100 = \% \text{ Force Relaxation}$$

The percent set is the percent elongation of the sample of the second cycle where the sample starts to resist the elongation. The percent set and the percent force relaxation are shown graphically also in FIGS. 7 and 15. The average percent force relaxation and percent set for three samples is reported for each maximum percent elongation value tested.

Tensile Test

The tensile test is used for measuring force versus percent elongation properties and percent available stretch of a material. The tests are performed on an Instron Model 1122, available from Instron Corporation of Canton, Mass. which is interfaced to a Gateway 2000 486/33 Hz computer available from Gateway 2000 of N. Sioux City, S. Dak., using TestWorks™ software which is available from Sintech, Inc. of Research Triangle Park, N.C. All essential parameters needed for testing are input in the TestWorks™ software for each test. Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device designed to cut a precise 1" wide sample. (If there is more than one direction of extensibility of the material, samples should be taken parallel to each ). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gage length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

The percent available stretch is the point at which there is an inflection in the force-elongation curve, beyond which point there is a rapid increase in the amount of force required to elongate the sample further. The average of the percent available stretch for three samples is recorded.

While the Test Methods described above are usable for many of the web materials of the present invention, it is recognized that the Test Methods may have to be modified to accommodate some of the more complex SELF web materials within the scope of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a chassis assembly having lateral edges and leg edges, said chassis assembly comprising a topsheet, a backsheet joined with said topsheet, and an absorbent core positioned between said topsheet and said backsheet, said absorbent core having side edges and waist edges; and
   a pair of side panels each comprising a separate member joined to said chassis assembly and extending laterally outwardly beyond one of said leg edges, at least a portion of each said side panel consisting of a structural elastic-like film web without the use of an elastic member, said web comprising a strainable network having a first region and a second region formed of substantially the same material composition, said first region providing a first, elastic-like resistive force to an applied axial elongation, and said second region providing a second distinctive resistive force to further applied axial elongation, thereby providing at least two stages of resistive forces in use.

2. The absorbent article of claim 1 wherein said absorbent article additionally comprises an extensible waist belt joined to said chassis assembly adjacent one of said lateral edges.

3. The absorbent article of claim 2 wherein said waist belt has a central waist panel.

4. The absorbent article of claim 3 wherein said chassis assembly additionally comprises an end flap extending longitudinally outwardly from one of said waist edges of said absorbent core, at least said end flap forming said central waist panel.

5. The absorbent article of claim 1 wherein said web comprises a laminate of two or more layers.

6. The absorbent article of claim 1 wherein said web exhibits a Poisson lateral contraction effect less than about 0.4 at 20% elongation as measured perpendicular to said applied axial elongation.

7. The absorbent article of claim 6 wherein said web exhibits a Poisson lateral contraction effect less than about 0.4 at 60% elongation as measured perpendicular to said applied axial elongation.

8. The absorbent article of claim 1 wherein said first region undergoes a substantially molecular-level deformation and said second region initially undergoes a substantially geometric deformation when said web material is subjected to an applied axial elongation.

9. The absorbent article of claim 1 wherein said web comprises a plurality of strainable networks.

10. The absorbent article of claim 1 wherein said web comprises a transition region.

11. A disposable absorbent article comprising:
    a chassis assembly having lateral edges and leg edges, said chassis assembly comprising a liquid pervious topsheet, a liquid impervious backsheet joined with said topsheet, and an absorbent core positioned between said topsheet and said backsheet, said absorbent core having side edges and waist edges; and
    a pair of side panels each comprising a separate member joined to said chassis assembly and extending laterally outwardly beyond one of said leg edges, at least a portion of each said side panel consisting of a structural elastic-like film web without the use of an elastic member, said web comprising a strainable network, said strainable network including at least a first region and a second region comprised of substantially the same material composition, said first region undergoing a substantially molecular-level deformation and said second region initially undergoing a substantially geometric definition when said web material is subjected to an applied axial elongation whereby said first region provides a first, elastic-like resistive force to an applied axial elongation, and said second region provides a second distinctive resistive force to further applied axial elongation, thereby providing at least two stages of resistive forces in use.

12. The absorbent article of claim 11 wherein said absorbent article additionally comprises an extensible waist belt joined to said chassis assembly adjacent one of said lateral edges.

13. The absorbent article of claim 11 wherein said web comprises a laminate of two or more layers.

14. The absorbent article of claim 13 wherein said web comprises an inner layer of a nonwoven material and an outer layer of a polymeric film.

15. The absorbent article of claim 14 wherein said web additionally comprises a support layer positioned between said outer layer and said inner layer.

16. The absorbent article of claim 11 wherein said web exhibits a Poisson lateral contraction effect less than about 0.4 at 20% elongation as measured perpendicular to said applied axial elongation.

17. The absorbent article of claim 11 wherein said first and second regions are substantially nonparallel to one another.

18. The absorbent article of claim 17 wherein said first region and said second regions are substantially linear.

19. The absorbent article of claim 11 wherein said web comprises a plurality of strainable networks.

* * * * *

UNITED STATES PATENT AND TRADEMARK OFFICE
CERTIFICATE OF CORRECTION

PATENT NO. : 5,876,391
DATED : March 2, 1999
INVENTOR(S) : DONALD C. ROE, et al.

It is certified that error appears in the above-identified patent and that said Letters Patent is hereby corrected as shown below:

Cover page, line 12 of the ABSTRACT, delete "contorting" and insert therefor -- contouring --.

Column 2, line 31, delete "contorting" and insert therefor -- contouring --.

Column 11, line 44, delete "contorting" and insert therefor -- contouring --.

Signed and Sealed this

First Day of August, 2000

Attest:

Attesting Officer

Q. TODD DICKINSON

Director of Patents and Trademarks